United States Patent
Takatsuji et al.

(10) Patent No.: US 9,434,958 B2
(45) Date of Patent: Sep. 6, 2016

(54) COMPLEX DISEASE RESISTANT MONOCOT HAVING OPTIMIZED AGRONOMIC CHARACTERISTICS

(75) Inventors: Hiroshi Takatsuji, Ibaraki (JP); Shingo Goto, Ibaraki (JP)

(73) Assignee: NATIONAL INSTITUTE OF AGROBIOLOGICAL SCIENCES, Ibaraki (JP)

(*) Notice: Subject to any disclaimer, the term of this patent is extended or adjusted under 35 U.S.C. 154(b) by 116 days.

(21) Appl. No.: 14/004,143

(22) PCT Filed: Mar. 1, 2012

(86) PCT No.: PCT/JP2012/055192
§ 371 (c)(1),
(2), (4) Date: Sep. 9, 2013

(87) PCT Pub. No.: WO2012/121093
PCT Pub. Date: Sep. 13, 2012

(65) Prior Publication Data
US 2014/0283209 A1    Sep. 18, 2014

(30) Foreign Application Priority Data

Mar. 10, 2011    (JP) .................. 2011-052531

(51) Int. Cl.
  C07K 14/145    (2006.01)
  C12N 15/82     (2006.01)
  C07K 14/415    (2006.01)
(52) U.S. Cl.
  CPC ......... *C12N 15/8279* (2013.01); *C07K 14/415* (2013.01); *C12N 15/8281* (2013.01); *C12N 15/8282* (2013.01)

(58) Field of Classification Search
  CPC .................................................... C12N 15/82
  See application file for complete search history.

(56) References Cited

U.S. PATENT DOCUMENTS

| | | | |
|---|---|---|---|
| 6,528,701 B1* | 3/2003 | Wang ................ | C12N 15/8237 435/320.1 |
| 2004/0133949 A1* | 7/2004 | Tanaka .............. | C12N 15/8229 800/288 |

(Continued)

FOREIGN PATENT DOCUMENTS

| EP | 0360750 A2 | 3/1990 |
|---|---|---|
| EP | 0431829 A1 | 6/1991 |

(Continued)

OTHER PUBLICATIONS

Os03g0177400 Os03g0177400 Oryza sativa Japonica—NCBI, published Jun. 8, 2010.*

(Continued)

*Primary Examiner* — Amjad Abraham
*Assistant Examiner* — Weihua Fan
(74) *Attorney, Agent, or Firm* — Fenwick & West LLP

(57) ABSTRACT

The present inventors isolated many promoters having various expression characteristics from monocots, connected the OsWRKY45 gene downstream of these promoters, and then re-introduced them into a monocot (rice plant), and thereby strived to produce a rice line having both complex disease resistance and excellent agronomic traits. As a result, the present inventors succeeded in producing transgenic plants having both disease resistance and good agronomic traits by expressing OsWRKY45 using upstream sequences of the EF1α or OsUbi7 gene as promoters.

15 Claims, 6 Drawing Sheets

(56) References Cited

U.S. PATENT DOCUMENTS

| | | | | |
|---|---|---|---|---|
| 2010/0122374 | A1* | 5/2010 | Takatsuji | A01N 65/40 800/279 |
| 2014/0208458 | A1* | 7/2014 | Takatsuji et al. | 800/279 |

FOREIGN PATENT DOCUMENTS

| | | | |
|---|---|---|---|
| JP | H 2-186925 | A | 7/1990 |
| JP | H 3-247220 | A | 11/1991 |
| JP | H 4-330233 | A | 11/1992 |
| JP | H 7-250685 | A | 10/1995 |
| JP | 2003-088379 | A | 3/2003 |
| JP | 2003-199448 | A | 7/2003 |
| JP | 2004-329215 | A | 11/2004 |
| WO | WO 2006/126671 | | 11/2006 |

OTHER PUBLICATIONS

Os09g0420800 Os09g0420800 Oryza sativa Japonica—NCBI, published Jun. 8, 2010.*
Shimono, Masaki, et al. "Rice WRKY45 plays a crucial role in benzothiadiazole-inducible blast resistance." The Plant Cell Online 19.6 (2007): 2064-2076.*
Tao, Zeng, et al. "A pair of allelic WRKY genes play opposite roles in rice-bacteria interactions." Plant Physiology 151.2 (2009): 936-948.*
Bahrini, I. et al., "Characterization of a Wheat Transcription Factor, TaWRKY45, and Its Effect on Fusarium Head Blight Resistance in Transgenic Wheat Plants," Breeding Science, 2011, pp. 121-129, vol. 61.
Chen, C., "Potentiation of Developmentally Regulated Plant Defense Response by AtWRKY18, a Pathogen-Induced Arabidopsis Transcription Factor," Plant Physiology, Jun. 2002, pp. 706-716, vol. 129.
Christensen, A.H. et al., "Ubiquitin Promoter-Based Vectors for High-Level Expression of Selectable and/or Screenable Marker Genes in Monocotyledonous Plants," Transgenic Research, 1996, pp. 213-218, vol. 5.
Chujo, T. et al., "Characterization of an Elicitor-Induced Rice WRKY Gene, OsWRKY71," Biosci. Biotechnol. Biochem., 2008, pp. 240-245, vol. 72, No. 1.
Chujo, T. et al., "Involvement of the Elicitor-Induced Gene OsWRKY53 in the Expression of Defense-Related Genes in Rice," Biochimica et Biophysica Acta, 2007, pp. 497-505, vol. 1769.
Kalde, M. et al., Members of the Arabidopsis WRKY Group III Transcription Factors Are Part of Different Plant Defense Signaling Pathways, MPMI, 2003, pp. 295-305, vol. 16, No. 4.
Li, J. et al., "The WRKY70 Transcription Factor: A Node of Convergence for Jasmonate-Mediated and Salicylate-Mediated Signals in Plant Defense," The Plant Cell, Feb. 2004, pp. 319-331. vol. 16.
Liu, X. et al., "OsWRKY71, a Rice Transcription Factor, is Involved in Rice Defense Response," Journal of Plant Physiology, 2007, pp. 969-979, vol. 164.
PCT International Search Report, PCT Application No. PCT/JP2012/055192, Apr. 10, 2012, 2 pages.
Qiu, D. et al., "OsWRKY13 Mediates Rice Disease Resistance by Regulating Defense- Related Genes in Salicylate- and Jasmonate-Dependent Signaling," MPMI, 2007, pp. 492-499, vol. 20, No. 5.
Qiu, Y. et al., "Cloning and Analysis of Expression Profile of 13 WRKY Genes in Rice," Chinese Science Bulletin, 2004, pp. 2159-2168, vol. 49, No. 20.
Qiu, Y. et al., "Over-Expression of the Stress-Induced OsWRKY45 Enhances Disease Resistance and Drought Tolerance in Arabidopsis," Environmental and Experimental Botany, 2009, pp. 35-47, vol. 65.
Robatzek, S. et al., "Targets of AtWRKY6 Regulation During Plant Senescence and Pathogen Defense," Genes & Development, 2002, pp. 1139-1149, vol. 16.
Shimono, M. et al., "Rice WRKY45 Plays a Crucial Role in Benzothiadiazole-Inducible Blast Resistance," The Plant Cell, Jun. 2007, pp. 2064-2076, vol. 19.
Sripriya, R. et al., "Generation of Selectable Marker-Free Sheath Blight Resistant Transgenic Rice Plants by Efficient Co-Transformation of a Cointegrate Vector T-DNA and a Binary Vector T-DNA in One Agrobacterium tumefaciences Strain," Plant Cell Rep., 2008, pp. 1635-1644, vol. 27.
Tao, Z. et al., "A Pair of Allelic WRKY Genes Play Opposite Roles in Rice-Bacteria Interactions," Plant Physiology, Oct. 2009, pp. 936-948, vol. 151.
Toki, S. et al., "Expression of a Maize Ubiquitin Gene Promoter-bar Chimeric Gene in Transgenic Rice Plants," Plant Physiol., 1992, pp. 1503-1507, vol. 100.
Windhövel, U. et al., "Expression of Erwinia uredovora Phytoene Desaturase in Synechococcus PCC7942 Leading to Resistance Against a Bleaching Herbicide," Plant Physiol., 1994, pp. 119-125, vol. 104.
Xie, Z. et al., "Annotations and Functional Analyses of the Rice WRKY Gene Superfamily Reveal Positive and Negative Regulators of Abscisic Acid Signaling in Aleurone Cells," Plant Physiology, Jan. 2005, pp. 176-189, vol. 137.
Yu, D. et al., "Evidence for an Important Role of WRKY DNA Binding Proteins in the Regulation of NPR1 Gene Expression," The Plant Cell, Jul. 2001, pp. 1527-1539, vol. 13.

* cited by examiner

SEQUENCE LISTING

```
<160> NUMBER OF SEQ ID NOS: 13

<210> SEQ ID NO 1
<211> LENGTH: 1453
<212> TYPE: DNA
<213> ORGANISM: Oryza sativa

<400> SEQUENCE: 1
gggtgctttg agctccatca ccagctgagc tgcgaggaag agagagtgcg agagtgcgcg      60
gcagcggcag tgtagtgtca gtcactgggt gtgcgcttgc ttgcttggat tgaggatgac     120
gtcatcgatg tcgccggcgc cggcgccggc gtacgcgcag gtgatggagg acatggagaa     180
ggggaaggag ctggcggcgc agctgcaggg gctcctccgc gactcgccgg aggccggccg     240
cttcgtcgac cagattctcc acaccttctc ccgggcgatg cgggcgctcg acaaggcggc     300
ggtctccgcc gccggaggag aagggtcgga ggtgcagagc gaggtcacct gcggggggcgg     360 ggccagcgcc ggcgggaaga ggaaagcccc cgccgccgac cggaaggcca actgccgcag     420
gaggacgcag caatcgtccg ggaattcggt ggtcgtcaag aacctcgacg acggccaggc     480
atggcgcaag tacgggcaga aggagatcca aaactccaag cacccaaagg cctacttccg     540
gtgcacgcac aagtacgacc agctgtgcac ggcgcagcgg caggtgcagc gctgcgacga     600
cgacccggcg agctacaggg tcacctacat cggcgagcac acctgccggg accggccac     660 cgcccccatc atcgcggcgc acgtcatcca ccaggtcgcc gccggcgaca acgacgacgg     720
ctgcggcggc ctccaagcgg ggtcccgcct catcagcttc gtcgccgcgc cggcggcgcc     780
agtagacgct gccgcggcgc cgacgaccag cacgatcacc acggtcaccg cgccgggccc     840
gctgctgcag ccgctcaagg tggagggcgg cgtcggctcg tccgaccagg aggaggtgct     900
gagcagcctc acgcccggca gctccgcggc gcgcggcggc ggcggcggcg cggagtcgc     960 gggtcccttc gggccggacc agggcgatgt cacgtcctcc ctgcactgga gctacgacgc    1020
```

-continued

```
cgtcgccggc atggagttct tcaagaacga cgaggttgtc ttcgatctgg acgacattat    1080
gggtttgagc ttttgatcac cgaagaatca tggatggaca cgggccgggt aaaacgatcg    1140
aaagaagatg gattccacgc gtgtgtacag aaataattag cggcagcgcg gatcttaatt    1200
tggaacttgc aaagatactc ctaattagcc tggctagatt agtttgtaaa ttccttgttg    1260
atgtgtcgtc tcagctttaa gctgcagaca tgctagcaag taacaacacg attagtacgt    1320
agtaatgtgg ttcttgatta tgagctgggg gtcttaacct tttttgtgtg acaagcaaga    1380
gaagaggatt tgggtacaat gtaatcctgt tcttccgctt tcgaaaaaaa aaacatata     1440 gcttcacgtg cct                                                       1453
```

<210> SEQ ID NO 2
<211> LENGTH: 326
<212> TYPE: PRT
<213> ORGANISM: Oryza sativa

<400> SEQUENCE: 2

```
Met Thr Ser Ser Met Ser Pro Ala Pro Ala Pro Ala Tyr Ala Gln Val
1               5                   10                  15

Met Glu Asp Met Glu Lys Gly Lys Glu Leu Ala Ala Gln Leu Gln Gly
            20                  25                  30

Leu Leu Arg Asp Ser Pro Glu Ala Gly Arg Phe Val Asp Gln Ile Leu
        35                  40                  45

His Thr Phe Ser Arg Ala Met Arg Ala Leu Asp Lys Ala Ala Val Ser
    50                  55                  60

Ala Ala Gly Gly Glu Gly Ser Glu Val Gln Ser Glu Val Thr Cys Gly
65                  70                  75                  80

Gly Gly Ala Ser Ala Gly Gly Lys Arg Lys Ala Pro Ala Ala Asp Arg
                85                  90                  95

Lys Ala Asn Cys Arg Arg Arg Thr Gln Gln Ser Ser Gly Asn Ser Val
            100                 105                 110

Val Val Lys Asn Leu Asp Asp Gly Gln Ala Trp Arg Lys Tyr Gly Gln
        115                 120                 125

Lys Glu Ile Gln Asn Ser Lys His Pro Lys Ala Tyr Phe Arg Cys Thr
    130                 135                 140

His Lys Tyr Asp Gln Leu Cys Thr Ala Gln Arg Gln Val Gln Arg Cys
145                 150                 155                 160

Asp Asp Asp Pro Ala Ser Tyr Arg Val Thr Tyr Ile Gly Glu His Thr
                165                 170                 175

Cys Arg Asp Pro Ala Thr Ala Pro Ile Ile Ala Ala His Val Ile His
            180                 185                 190

Gln Val Ala Ala Gly Asp Asn Asp Asp Gly Cys Gly Gly Leu Gln Ala
        195                 200                 205

Gly Ser Arg Leu Ile Ser Phe Val Ala Ala Pro Ala Ala Pro Val Asp
    210                 215                 220

Ala Ala Ala Ala Pro Thr Thr Ser Thr Ile Thr Thr Val Thr Ala Pro
225                 230                 235                 240

Gly Pro Leu Leu Gln Pro Leu Lys Val Glu Gly Val Gly Ser Ser
                245                 250                 255

Asp Gln Glu Glu Val Leu Ser Ser Leu Thr Pro Gly Ser Ser Ala Ala
            260                 265                 270

Arg Gly Gly Gly Gly Gly Gly Val Ala Gly Pro Phe Gly Pro Asp
        275                 280                 285

Gln Gly Asp Val Thr Ser Ser Leu His Trp Ser Tyr Asp Ala Val Ala
```

```
          290                 295                 300
Gly Met Glu Phe Phe Lys Asn Asp Glu Val Val Phe Asp Leu Asp Asp
305                 310                 315                 320

Ile Met Gly Leu Ser Phe
                325
```

<210> SEQ ID NO 3
<211> LENGTH: 2042
<212> TYPE: DNA
<213> ORGANISM: Oryza sativa

<400> SEQUENCE: 3

| | | | | | |
|---|---|---|---|---|---|
| attgctcttc | gaatcaccac | attaccagtg | gtgaatgtac | aagatgctgt | caaactctct | 60 |
| ctgtaaatct | ttttaccggt | gcatgttgct | tcagttttct | ggtcacattg | cgtgcttggc | 120 |
| gtactgccat | acacaatgca | gtggtgctgg | gcttgttgca | tttgtgctct | tcgtgcggat | 180 |
| gccgtggatt | ctggcacttt | tccaatatgt | atatttctta | taaaaaaaac | tcactttttcc | 240 |
| aacatcaggg | tcgcgtggtt | tgtaagcatt | tcggttcgat | tctgtagtct | ccagttttgc | 300 |
| ttttattcc | tcctttttta | tattccaaat | gattttgtgg | aaattgtggc | agaggattgc | 360 |
| ctcaaggttc | ctcactgctg | tctcatgcat | gcatcatcca | actgcatcgc | catcgtttcg | 420 |
| tttatgctta | tcttgccatc | gtttcgctta | tatttagctt | tatccatact | gtttatgtag | 480 |
| tcaaataaa | atctatggat | aaaattttta | tatgcatgtc | tttagggatt | caaaaataaa | 540 |
| ttgtgtaaaa | taaagtaggg | tgaaaaaaaa | atactaaatc | aactctaaaa | ttaagtttga | 600 |
| aaaaataaat | tttagcttac | aatcataagc | ataagcacaa | atgaacgatg | gatgcaccaa | 660 |
| tagagtcaat | atgattatta | aatgatttac | ttcttgttaa | tttagcggta | ataaaagaat | 720 |
| attcgctccg | tcccaaagta | gatatcactt | taggattcaa | aaattgtccc | aaaaagcttg | 780 |
| tcactttaaa | gttcatatttt | gtcatatcaa | tcacatcaaa | tcaaaatttt | ctccattcta | 840 |
| ctctctgcct | accaaccata | tattccctcc | gtttcataat | gtaagtcatt | ctagcatttc | 900 |
| ctacattcat | attgatgtta | ttgaatctag | acatatatat | ctatctatat | tcattaacat | 960 |
| caatatgaat | gtgggaaatg | ctagaatgac | ttatattgtg | aaacggagga | agtatcattt | 1020 |
| aatagagagt | attatactac | ctccgtttca | ggttataaga | cttttctagca | ttgcccgcat | 1080 |
| tcatatatgt | gttaatgaat | ctaggcacat | atatgtctag | attcattaat | atatatatat | 1140 |
| atatatatat | atatatatat | atatgaatat | gggcaatact | agaaagtctt | ataatgtgaa | 1200 |
| acggaataag | tagtcatttt | tgctaaatag | agagtattag | cagagaagga | tgataggtat | 1260 |
| attgggatgg | aggtagtagt | atagtagcct | cggaaatatc | tacagcaatc | taaccttgtg | 1320 |
| gaaattata | catatgaggt | tccgtaacac | gatgtgaatt | cagttatata | agaaagatt | 1380 |
| tctttaaact | tgtcattact | cttcccatcc | tagatgagac | gtatcctaga | ttattatatt | 1440 |
| ttagaacgga | gttagaatta | ttatgccacg | cttacaatct | cttaaaactt | tctaaatcaa | 1500 |
| accttacttc | aataattctt | taagctattt | attaactttg | tcatatttgt | tccatttata | 1560 |
| cgactaattt | ttctgtctac | aatttatcca | attatcctgt | cggaccccgt | cctctgaaaa | 1620 |
| caaatcatcc | tagcaacaag | atctacttat | caccgagcgc | gaatcttaaa | gctttagagt | 1680 |
| atcagagtca | gaaactgatc | accaggcgtg | aatcttaaag | cgaaagcgag | ccgaaaacag | 1740 |
| ggatataatc | cgaacaataa | ccaaagccac | caaaaaacgt | gaaaagtaat | tgaaaaccta | 1800 |
| gtttacccgc | accgtccgat | ctcccgagac | gactcgccga | ccaccgtccg | ttctacctat | 1860 |
| aaatccacgc | ggcccgagcc | accgaaaaat | ccagccaaga | ggggaaaaaa | aaagggaagg | 1920 |

```
aatttttttc ttttttttttt gttcgcctcc gcttcttcct cacgcagctc tcgcctcgcc    1980
tcgccgcccg ccactagaga ggagagggag aaggaggagg aggcaaatcc cagcaaaaga    2040
ag                                                                   2042
```

<210> SEQ ID NO 4
<211> LENGTH: 3559
<212> TYPE: DNA
<213> ORGANISM: Artificial
<220> FEATURE:
<223> OTHER INFORMATION: An artificially synthesized nucleotide sequence

<400> SEQUENCE: 4

```
attgctcttc gaatcaccac attaccagtg gtgaatgtac aagatgctgt caaactctct      60
ctgtaaatct ttttaccggt gcatgttgct tcagttttct ggtcacattg cgtgcttggc    120
gtactgccat acacaatgca gtggtgctgg gcttgttgca tttgtgctct tcgtgcggat    180
gccgtggatt ctggcacttt tccaatatgt atatttctta taaaaaaaac tcactttttcc    240 aacatcaggg tcgcgtggtt tgtaagcatt tcggttcgat tctgtagtct ccagttttgc    300
tttttattcc tcctttttta tattccaaat gattttgtgg aaattgtggc agaggattgc    360
ctcaaggttc ctcactgctg tctcatgcat gcatcatcca actgcatcgc catcgtttcg    420
tttatgctta tcttgccatc gtttcgctta tatttagctt tatccatact gtttatgtag    480
tcaaaataaa atctatggat aaaattttta tatgcatgtc tttagggatt caaaaataaa    540
ttgtgtaaaa taaagtaggg tgaaaaaaaa atactaaatc aactctaaaa ttaagtttga    600
aaaaataaat tttagcttac aatcataagc ataagcacaa atgaacgatg gatgcaccaa    660
tagagtcaat atgattatta aatgatttac ttcttgttaa tttagcggta ataaaagaat    720
attcgctccg tcccaaagta gatatcactt taggattcaa aaattgtccc aaaaagcttg    780
tcactttaaa gttcatattt gtcatatcaa tcacatcaaa tcaaaatttt ctccattcta    840
ctctctgcct accaaccata tattccctcc gtttcataat gtaagtcatt ctagcatttc    900
ctacattcat attgatgtta ttgaatctag acatatatat ctatctatat tcattaacat    960
caatatgaat gtgggaaatg ctagaatgac ttatattgtg aaacggagga agtatcattt   1020
aatagagagt attatactac ctccgtttca ggttataaga cttttctagca ttgcccgcat   1080 tcatatatgt gttaatgaat ctaggcacat atatgtctag attcattaat atatatatat   1140
atatatatat atatatatat atatgaatat gggcaatact agaaagtctt ataatgtgaa   1200
acggaataag tagtcatttt tgctaaatag agagtattag cagagaagga tgataggtat   1260
attgggatgg aggtagtagt atagtagcct cggaaatatc tacagcaatc taaccttgtg   1320
gaaatttata catatgaggt tccgtaacac gatgtgaatt cagttatata agaaagatt    1380 tcttttaaact tgtcattact cttcccatcc tagatgagac gtatcctaga ttattatatt   1440
ttagaacgga gttagaatta ttatgccacg cttacaatct cttaaaactt tctaaatcaa    1500
accttacttc aataattctt taagctattt attaactttg tcatatttgt tccatttata   1560
cgactaattt ttctgtctac aatttatcca attatcctgt cggacccggt cctctgaaaa    1620
caaatcatcc tagcaacaag atctacttat caccgagcgc gaatcttaaa gctttagagt   1680
atcagagtca gaaactgatc accaggcgtg aatcttaaag cgaaagcgag ccgaaaacag    1740
ggatataatc cgaacaataa ccaaagccac caaaaaacgt gaaaagtaat tgaaaaccta   1800
gtttacccgc accgtccgat ctcccgagac gactcgccga ccaccgtccg ttctacctat    1860
```

```
aaatccacgc ggcccgagcc accgaaaaat ccagccaaga ggggaaaaaa aaagggaagg      1920 aattttttc tttttttttt gttcgcctcc gcttcttcct cacgcagctc tcgcctcgcc       1980
tcgccgcccg ccactagaga ggagagggag aaggaggagg aggcaaatcc cagcaaaaga      2040
agaagcttgg ccaaatcggc cgagctcgaa ttcgtcgagc tctatttagg tgacactata      2100
gaaccagggt gctttgagct ccatcaccag ctgagctgcg aggaagagag agtgcgagag      2160
tgcgcggcag cggcagtgta gtgtcagtca ctgggtgtgc gcttgcttgc ttggattgag      2220
gatgacgtca tcgatgtcgc cggcgccggc gccggcgtac gcgcaggtga tggaggacat      2280
ggagaagggg aaggagctgg cggcgcagct gcagggctc ctccgcgact cgccggaggc       2340
cggccgcttc gtcgaccaga ttctccacac cttctcccgg gcgatgcggg cgctcgacaa      2400
ggcggcggtc tccgccgccg gaggagaagg gtcggaggtg cagagcgagg tcacctgcgg      2460
gggcggggcc agcgccggcg ggaagaggaa agccccccgcc gccgaccgga aggccaactg    2520
ccgcaggagg acgcagcaat cgtccgggaa ttcgtggtc gtcaagaacc tcgacgacgg       2580
ccaggcatgg cgcaagtacg ggcagaagga gatccaaaac tccaagcacc caaaggccta     2640
cttccggtgc acgcacaagt acgaccagct gtgcacggcg cagcggcagg tgcagcgctg     2700
cgacgacgac ccggcgagct acagggtcac ctacatcggc gagcacacct gccgggaccc     2760
ggccaccgcc cccatcatcg cggcgcacgt catccaccag gtcgccgccg gcgacaacga     2820
cgacggctgc ggcggcctcc aagcggggtc ccgcctcatc agcttcgtcg ccgcgccggc     2880
ggcgccagta gacgctgccg cggcgccgac gaccagcacg atcaccacgg tcaccgcgcc    2940 gggccccgctg ctgcagccgc tcaaggtgga gggcggcgtc ggctcgtccg accaggagga   3000
ggtgctgagc agcctcacgc ccggcagctc cgcggcgcgc ggcggcggcg gcggcggcgg     3060
agtcgcgggt cccttcgggc cggaccaggg cgatgtcacg tcctccctgc actggagcta     3120
cgacgccgtc gccggcatgg agttcttcaa gaacgacgag gttgtcttcg atctggacga     3180
cattatgggt ttgagctttt gatcaccgaa gaatcatgga tggacacggg ccgggtaaaa     3240
cgatcgaaag aagatggatt ccacgcgtgt gtacagaaat aattagcggc agcgcggatc     3300
ttaatttgga acttgcaaag atactcctaa ttagcctggc tagattagtt tgtaaattcc     3360
ttgttgatgt gtcgtctcag ctttaagctg cagacatgct agcaagtaac aacacgatta    3420
gtacgtagta atgtgttct tgattatgag ctggggtct taacctttt tgtgtgacaa       3480 gcaagagaag aggatttggg tacaatgtaa tcctgttctt ccgctttcga aaaaaaaaa    3540 catatagctt cacgtgcct                                                   3559
```

<210> SEQ ID NO 5
<211> LENGTH: 2022
<212> TYPE: DNA
<213> ORGANISM: Oryza sativa
<400> SEQUENCE: 5

```
agccttttgg agagggacta ctcatgatgt ttgactcact taaattgcaa catattactt       60
gggttacact aaggaaaatc tgcaagtgta tccttttttg gctgttctgt cacaaggaaa      120
tgaaattctt gccgatgtga aaattatttt tttggcagac aactcctggt taagctttaa      180
gctaaacagt aagtagatga acagcactgt agatacatgt ttaagtgaat ttagtttcct      240
gcaataggca taaatgttta actcttctat ggaggagcat taactgttag ccgcattagc      300
ctgacttatt tgatttttag catctgaaat agtggaattt ggagatgact tatttgatat      360
ttgttgcagg cttcttgatg ttttgctgat aacccttcga cactgtatgg tcacccagat      420
```

```
tgtctgcgag cctgaagacc tcaactgatc atcctgcgtg cactagtcta agctacttgg      480
ctaacaaaac tatgttaccc tgaattttgt gtatatatat gacgtgttag tcactcccag      540
gagaactcat atgggcagag atcaccggat acttttcata gtcgcataga atcctgtagc      600
tagccaaact gccagagtca tgagctgacg cctatagttg caattacagt actaccaagt      660
ttttgttggc tctcccttct catgtctgtg cattctgtaa agatggtttt gccgctagca      720
aaagtatgat ggttcggatt tttattcttg ttctgctgat ccatgaattt ccagttcctg      780
gtacgagttt caggttgtcg tgtttgcaaa tttgtttcag gactcgggag tacgcaggag      840
attaccgagt gatagaattt cgccacttaa agagaaagac agctgtgctg ggaatctggg      900
acatgaataa aatgaaattg taaataaagt atctgctata caatccgcac tatgagagct      960
tattcatatg tgtttatata gttgagtgca cacgtatatt tgagagttta tgtgcttata     1020
cagatgagtg cacatgttat ttgagagttt gcgtttgtag tgtatttcga ttttttttaaa    1080 aaaaagaaat caataaggga gtctaccggt agagaggcga aaacattgat ttttcaccag     1140
cgaggagata aaccttgtaa acctttttct ctaatccaaa aacaaacttg aattatgtgt     1200
acttacttgc gccctgcgaa acctcccgag acttaaacgt aacgcaaacg tttgaacagg     1260
ctgaccgcag gattaacatc gaacgatcaa tactgcaacg caacaacaac catcagacaa     1320
agatcggacg gctaggaagg aaccctagca cccgtgagtg cctatataag agacaatcct     1380
ctcgccctaa tccctcccct ctcccatctc accccgccgc cgccgccgcc gcagcctcct     1440
caaggctgct cccatcctct ccttcgaggt cagctgcaga tcttctctct tctccttgtt     1500
tgcgccggtt catggtagtt cgtagccgta gatctgattc gatggagcga ggtttgggtg     1560
atttgatgcc tgggcatgtt gtttttgtcc attattagta actttttctg tgtattcgtc     1620
tcactgctat gatcttagtt tgctgttcgt tgacgcgatg atttattgac ttgtcggtga     1680
atcatttatg tacgttgaaa attatcggta gaatcggact attaacttga tgtgctgcag     1740
aatcatgtac ataagttgaa aatcatcggt agaatcagta gaagtatttc tatctagaat     1800
ccgttcgaat atctctgttt ttatgttcga atagatggtg ttatcgtcta tgcctggttc     1860
ggtttggtcg attactgcgc gttagcactt ataattgatg tcgaagttca tctgatctgt     1920
gagcttgcct gtaatattat ttggagttag aaattatgca cgcctgttgt ttctaatctt     1980
tgtttcgttc tgttttgcag ttagcttcct ccttattcaa cc                        2022
```

<210> SEQ ID NO 6
<211> LENGTH: 3539
<212> TYPE: DNA
<213> ORGANISM: Artificial
<220> FEATURE:
<223> OTHER INFORMATION: An artificially synthesized nucleotide sequence

<400> SEQUENCE: 6

```
agccttttgg agagggacta ctcatgatgt ttgactcact taaattgcaa catattactt       60
gggttacact aaggaaaatc tgcaagtgta tccttttttg gctgttctgt cacaaggaaa      120
tgaaattctt gccgatgtga aaattatttt tttggcagac aactcctggt taagctttaa      180
gctaaacagt aagtagatga acagcactgt agatacatgt ttaagtgaat ttagtttcct      240
gcaataggca taaatgttaa actcttctat ggaggagcat taactgttag ccgcattagc      300
ctgactattt tgattttag catctgaaat agtggaattt ggagatgact tatttgatat       360
ttgttgcagg cttcttgatg ttttgctgat aacccttcga cactgtatgg tcacccagat      420
```

```
tgtctgcgag cctgaagacc tcaactgatc atcctgcgtg cactagtcta agctacttgg    480
ctaacaaaac tatgttaccc tgaattttgt gtatatatat gacgtgttag tcactcccag    540
gagaactcat atgggcagag atcaccggat acttttcata gtcgcataga atcctgtagc    600
tagccaaact gccagagtca tgagctgacg cctatagttg caattacagt actaccaagt    660
ttttgttggc tctcccttct catgtctgtg cattctgtaa agatggtttt gccgctagca    720
aaagtatgat ggttcggatt tttattcttg ttctgctgat ccatgaattt ccagttcctg    780
gtacgagttt caggttgtcg tgtttgcaaa tttgtttcag gactcgggag tacgcaggag    840
attaccgagt gatagaattt cgccacttaa agagaaagac agctgtgctg ggaatctggg    900
acatgaataa aatgaaattg taaataaagt atctgctata caatccgcac tatgagagct    960
tattcatatg tgtttatata gttgagtgca cacgtatatt tgagagttta tgtgcttata   1020
cagatgagtg cacatgttat ttgagagttt gcgtttgtag tgtatttcga ttttttttaaa  1080
aaaaagaaat caataaggga gtctaccggt agagaggcga aaacattgat ttttcaccag   1140
cgaggagata aaccttgtaa acctttttct ctaatccaaa acaaacttg aattatgtgt    1200
acttacttgc gccctgcgaa acctcccgag acttaaacgt aacgcaaacg tttgaacagg   1260
ctgaccgcag gattaacatc gaacgatcaa tactgcaacg caacaacaac catcagacaa   1320
agatcggacg gctaggaagg aaccctagca cccgtgagtg cctatataag agacaatcct   1380
ctcgccctaa tccctcccct ctcccatctc accccgccgc cgccgccgcc gcagcctcct   1440
caaggctgct cccatcctct ccttcgaggt cagctgcaga tcttctctct tctccttgtt   1500
tgcgccggtt catggtagtt cgtagccgta gatctgattc gatggagcga ggtttgggtg   1560
atttgatgcc tgggcatgtt gttttttgtcc attattagta acttttttctg tgtattcgtc  1620
tcactgctat gatcttagtt tgctgttcgt tgacgcgatg attttattgac ttgtcggtga   1680
atcatttatg tacgttgaaa attatcggta gaatcggact attaacttga tgtgctgcag   1740
aatcatgtac ataagttgaa aatcatcggt agaatcagta gaagtatttc tatctagaat   1800
ccgttcgaat atctctgttt ttatgttcga atagatggtg ttatcgtcta tgcctggttc   1860
ggtttggtcg attactgcgc gttagcactt ataattgatg tcgaagttca tctgatctgt   1920
gagcttgcct gtaatattat ttggagttag aaattatgca cgcctgttgt ttctaatctt   1980
tgtttcgttc tgttttgcag ttagcttcct ccttattcaa ccaagcttgg ccaaatcggc   2040
cgagctcgaa ttcgtcgagc tctatttagg tgacactata gaaccagggt gctttgagct   2100
ccatcaccag ctgagctgcg aggaagagag agtgcgagag tgcgcggcag cggcagtgta   2160
gtgtcagtca ctgggtgtgc gcttgcttgc ttggattgag gatgacgtca tcgatgtcgc   2220
cggcgccggc gccggcgtac gcgcaggtga tggaggacat ggagaagggg aaggagctgg   2280
cggcgcagct gcaggggctc ctccgcgact cgccggaggc cggccgcttc gtcgaccaga   2340
ttctccacac cttctcccgg gcgatgcggg cgctcgacaa gcggcggtc tccgccgccg    2400
gaggagaagg tcggaggtg cagagcgagg tcacctgcgg gggcgggcc agcgccggcg     2460
ggaagaggaa agcccccgcc gccgaccgga aggccaactg ccgcaggagg acgcagcaat   2520
cgtccggaa ttcggtggtc gtcaagaacc tcgacgacgg ccaggcatgg cgcaagtacg    2580
ggcagaagga gatccaaaac tccaagcacc caaaggccta cttccggtgc acgcacaagt   2640
acgaccagct gtgcacggcg cagcggcagg tgcagcgctg cgacgacgac ccggcgagct   2700
acaggggtcac ctcatcggc gagcacacct gccgggaccc ggccaccgcc ccatcatcg    2760
cggcgcacgt catccaccag gtcgccgccg gcgacaacga cgacggctgc ggcggcctcc   2820
```

| | | |
|---|---|---|
| aagcggggtc ccgcctcatc agcttcgtcg ccgcgccggc ggcgccagta gacgctgccg | 2880 | |
| cggcgccgac gaccagcacg atcaccacgg tcaccgcgcc gggcccgctg ctgcagccgc | 2940 | |
| tcaaggtgga gggcggcgtc ggctcgtccg accaggagga ggtgctgagc agcctcacgc | 3000 | |
| ccggcagctc cgcggcgcgc ggcggcggcg gcggcggcgg agtcgcgggt cccttcgggc | 3060 | |
| cggaccaggg cgatgtcacg tcctccctgc actggagcta cgacgccgtc gccggcatgg | 3120 | |
| agttcttcaa gaacgacgag gttgtcttcg atctggacga cattatgggt ttgagctttt | 3180 | |
| gatcaccgaa gaatcatgga tggacacggg ccgggtaaaa cgatcgaaag aagatggatt | 3240 | |
| ccacgcgtgt gtacagaaat aattagcggc agcgcggatc ttaatttgga acttgcaaag | 3300 | |
| atactcctaa ttagcctggc tagattagtt tgtaaattcc ttgttgatgt gtcgtctcag | 3360 | |
| ctttaagctg cagacatgct agcaagtaac aacacgatta gtacgtagta atgtggttct | 3420 | |
| tgattatgag ctgggggtct taaccttttt tgtgtgacaa gcaagagaag aggatttggg | 3480 | |
| tacaatgtaa tcctgttctt ccgctttcga aaaaaaaaaa catatagctt cacgtgcct | 3539 | |

<210> SEQ ID NO 7
<211> LENGTH: 1747
<212> TYPE: DNA
<213> ORGANISM: Oryza sativa

<400> SEQUENCE: 7

| | | |
|---|---|---|
| ctgatgatta ttttgttgat catgattttc ttttggctat ttgattttt gaaagatatt | 60 | |
| tttttccctg ggaagacacc tatgggacga agatattatg tttcttatat agcaccaaac | 120 | |
| aaatttaata tatatatata tatatatata tatatatata tatatatata tatatatata | 180 | |
| tatatatata tatatatata tatatatata tatcacatca gtctctgcac aaagtgcatc | 240 | |
| ctgggctgct tcaattataa agccccattc accacatttg ctagatagtc gaaaagcacc | 300 | |
| atcaatattg agcttcaggt attttttggtt gtgttgtggt tggattgatt ctaatatata | 360 | |
| ccaaatcaat ataattcact accaaaatat accatagcca tcacaacttt attaattttg | 420 | |
| gtagcttaag atggtatata taataaccaa ttaacaactg attctaatttt tactacggcc | 480 | |
| cagtatgtac caatacaaaa caacgagtat gttttcttcc atcgtaatcg tacacagtac | 540 | |
| aaaaaaacct ggccagcctt tcttgggctg gggctctctt tcgaaaggtc acaaaacgta | 600 | |
| cacggcagta acgccgcttc gctgcgtgtt aacggccacc aaccccgccg tgagcaaacg | 660 | |
| gcatcagctt tccacctcct cgatatctcc gcggcgccgt ctggacccgc cccctttccg | 720 | |
| ttcctttctt tccttctcgc gtttgcgtgg tggggacgga ctccccaaac cgcctctccc | 780 | |
| tctctccttt ctttatttgt ctatattctc actgggcccc acccaccgca ccctgggcc | 840 | |
| cactcacgag tccccccctc cccacctata aatacccccac ccctcctcg cctcttcctc | 900 | |
| cgtcaatcga accccaaaat cgcagagaaa aaaaatctc ccctcgaagc gaagcgtcga | 960 | |
| atcgccttct caaggtatgc gattttctga tcctctccgt tcctcgcgtt tgatttgatt | 1020 | |
| tcccggcctg ttcgtgattg tgagatgttg tggttagtct ccgttttgcg atctgtggta | 1080 | |
| gatttgaaca ggtttagatg gggttcgcgt ggtatgctgg atctgtgatt atgagcgatg | 1140 | |
| ctgttcgtgg tccaagtatt gattggttcg gatctagtag tagaactgtg ctagggttgt | 1200 | |
| gattcgttcc gatctgttca attagtagga tttagtctct gttttctcg ttgatccaag | 1260 | |
| tagcagcttc aggtatattt tgcttaggtt gttttgatt cagtccctct agttgcatag | 1320 | |
| attctactct gttcatgttt aatctaaggg ctgcgtcttg ttgattagtg attacatagc | 1380 | |

| | |
|---|---:|
| atagctttca ggatatttta cttgcttatg cctatcttat caactgttgc acctgtaaat | 1440 |
| tctagcctat gttataacct gccttatgtg ctctcgggat agtgctagta gttattgaat | 1500 |
| cagtttgccg atggatttct agtagttcat agacctgcat attattttg tgaacacgag | 1560 |
| cacggtgcgt ctctctattt tgttaggtca ctgttggtgt tgataggtac actgatgtta | 1620 |
| ttgtggttta ggtcgtgtat ctaacatatt ggataattt gattgactga tttctgctgt | 1680 |
| acttgcttgg tattgttata atttcatgtt catagttgct gaccatgctt cggtaattgt | 1740 |
| gtgtgca | 1747 |

<210> SEQ ID NO 8
<211> LENGTH: 3272
<212> TYPE: DNA
<213> ORGANISM: Artificial
<220> FEATURE:
<223> OTHER INFORMATION: An artificially synthesized nucleotide sequence

<400> SEQUENCE: 8

| | |
|---|---:|
| ctgatgatta ttttgttgat catgattttc ttttggctat ttgattttt gaaagatatt | 60 |
| tttttccctg ggaagacacc tatgggacga agatattatg tttcttatat agcaccaaac | 120 |
| aaatttaata tatatatata tatatatata tatatatata tatatatata tatatatata | 180 |
| tatatatata tatatatata tatatatata tatcacatca gtctctgcac aaagtgcatc | 240 |
| ctgggctgct tcaattataa agccccattc accacatttg ctagatagtc gaaaagcacc | 300 |
| atcaatattg agcttcaggt attttggtt gtgttgtggt tggattgatt ctaatatata | 360 |
| ccaaatcaat ataattcact accaaaatat accatagcca tcacaacttt attaatttg | 420 |
| gtagcttaag atggtatata taataaccaa ttaacaactg attctaattt tactacggcc | 480 |
| cagtatgtac caatacaaaa caacgagtat gttttcttcc atcgtaatcg tacacagtac | 540 |
| aaaaaaacct ggccagcctt tcttgggctg gggctctctt tcgaaaggtc acaaaacgta | 600 |
| cacggcagta acgccgcttc gctgcgtgtt aacggccacc aaccccgccg tgagcaaacg | 660 |
| gcatcagctt tccacctcct cgatatctcc gcggcgccgt ctggacccgc cccctttccg | 720 |
| ttcctttctt tccttctcgc gttttgcgtgg tggggacgga ctcccaaac cgcctctccc | 780 |
| tctctccttt ctttatttgt ctatattctc actgggcccc acccaccgca ccctgggcc | 840 |
| cactcacgag tccccccctc cccacctata aataccccac ccctcctcg cctcttcctc | 900 |
| cgtcaatcga accccaaaat cgcagagaaa aaaaaatctc ccctcgaagc gaagcgtcga | 960 |
| atcgccttct caaggtatgc gatttttctga tcctctccgt tcctcgcgtt tgatttgatt | 1020 |
| tcccggcctg ttcgtgattg tgagatgttg tggttagtct ccgttttgcg atctgtggta | 1080 |
| gatttgaaca ggtttagatg gggttcgcgt ggtatgctgg atctgtgatt atgagcgatg | 1140 |
| ctgttcgtgg tccaagtatt gattggttcg gatctagtag tagaactgtg ctagggttgt | 1200 |
| gattcgttcc gatctgttca attagtagga tttagtctct gttttctcg ttgatccaag | 1260 |
| tagcagcttc aggtatattt tgcttaggtt gttttttgatt cagtccctct agttgcatag | 1320 |
| attctactct gttcatgttt aatctaaggg ctgcgtcttg ttgattagtg attacatagc | 1380 |
| atagctttca ggatatttta cttgcttatg cctatcttat caactgttgc acctgtaaat | 1440 |
| tctagcctat gttataacct gccttatgtg ctctcgggat agtgctagta gttattgaat | 1500 |
| cagtttgccg atggatttct agtagttcat agacctgcat attattttg tgaacacgag | 1560 |
| cacggtgcgt ctctctattt tgttaggtca ctgttggtgt tgataggtac actgatgtta | 1620 |
| ttgtggttta ggtcgtgtat ctaacatatt ggataattt gattgactga tttctgctgt | 1680 |

-continued

```
acttgcttgg tattgttata atttcatgtt catagttgct gaccatgctt cggtaattgt    1740
gtgtgcagat ctctagagct tggccaaatc ggccgagctc gaattcgtcg agctctattt    1800
aggtgacact atagaaccag ggtgctttga gctccatcac cagctgagct gcgaggaaga    1860
gagagtgcga gagtgcgcgg cagcggcagt gtagtgtcag tcactgggtg tgcgcttgct    1920
tgcttggatt gaggatgacg tcatcgatgt cgccggcgcc ggcgccggcg tacgcgcagg    1980
tgatggagga catggagaag gggaaggagc tggcggcgca gctgcagggg ctcctccgcg    2040
actcgccgga ggccggccgc ttcgtcgacc agattctcca ccttctcc cgggcgatgc     2100 gggcgctcga caaggcggcg gtctccgccg ccggaggaga agggtcggag gtgcagagcg    2160
aggtcacctg cggggggcggg gccagcgccg gcgggaagag gaaagccccc gccgccgacc  2220
ggaaggccaa ctgccgcagg aggacgcagc aatcgtccgg gaattcggtg gtcgtcaaga   2280
acctcgacga cggccaggca tggcgcaagt acgggcagaa ggagatccaa aactccaagc   2340
acccaaaggc ctacttccgg tgcacgcaca agtacgacca gctgtgcacg gcgcagcggc   2400
aggtgcagcg ctgcgacgac gacccggcga gctacagggt cacctacatc ggcgagcaca   2460
cctgccggga cccggccacc gccccatca tcgcggcgca cgtcatccac caggtcgccg    2520
ccggcgacaa cgacgacggc tgcggcggcc tccaagcggg gtcccgcctc atcagcttcg   2580
tcgccgcgcc ggcggcgcca gtagacgctg ccgcggcgcc gacgaccagc acgatcacca   2640
cggtcaccgc gccgggcccg ctgctgcagc cgctcaaggt ggagggcggc gtcggctcgt   2700
ccgaccagga ggaggtgctg agcagcctca cgcccggcag ctccgcggcg cgcggcggcg   2760
gcggcggcgg cggagtcgcg ggtccccttcg ggccggacca gggcgatgtc acgtcctccc  2820
tgcactggag ctacgacgcc gtcgccggca tggagttctt caagaacgac gaggttgtct   2880
tcgatctgga cgacattatg ggtttgagct tttgatcacc gaagaatcat ggatggacac    2940
gggccgggta aaacgatcga aagaagatgg attccacgcg tgtgtacaga aataattagc   3000
ggcagcgcgg atcttaattt ggaacttgca aagatactcc taattagcct ggctagatta   3060
gtttgtaaat tccttgttga tgtgtcgtct cagctttaag ctgcagacat gctagcaagt   3120
aacaacacga ttagtacgta gtaatgtggt tcttgattat gagctggggg tcttaacctt   3180
ttttgtgtga caagcaagag aagaggattt gggtacaatg taatcctgtt cttccgcttt   3240
cgaaaaaaaa aaacatatag cttcacgtgc ct                                 3272
```

<210> SEQ ID NO 9
<211> LENGTH: 13
<212> TYPE: DNA
<213> ORGANISM: Artificial
<220> FEATURE:
<223> OTHER INFORMATION: An artificially synthesized nucleotide sequence

<400> SEQUENCE: 9
agcttggcca aat                                                         13

<210> SEQ ID NO 10
<211> LENGTH: 21
<212> TYPE: DNA
<213> ORGANISM: Artificial
<220> FEATURE:
<223> OTHER INFORMATION: An artificially synthesized nucleotide sequence

<400> SEQUENCE: 10
agctggcgcg ccatttaaat a                                                21

```
<210> SEQ ID NO 11
<211> LENGTH: 21
<212> TYPE: DNA
<213> ORGANISM: Artificial
<220> FEATURE:
<223> OTHER INFORMATION: An artificially synthesized nucleotide sequence

<400> SEQUENCE: 11
agcttattta aatggcgcgc c                                             21

<210> SEQ ID NO 12
<211> LENGTH: 24
<212> TYPE: DNA
<213> ORGANISM: Artificial
<220> FEATURE:
<223> OTHER INFORMATION: An artificially synthesized primer sequence

<400> SEQUENCE: 12
tgtgtgacaa gcaagagaag agga                                          24

<210> SEQ ID NO 13
<211> LENGTH: 20
<212> TYPE: DNA
<213> ORGANISM: Artificial
<220> FEATURE:
<223> OTHER INFORMATION: An artificially synthesized primer sequence

<400> SEQUENCE: 13
aacgatcggg gaaattcgag                                               20
```

COMPLEX DISEASE RESISTANT MONOCOT HAVING OPTIMIZED AGRONOMIC CHARACTERISTICS

TECHNICAL FIELD

The present invention relates to: nucleic acid constructs that comprise a polynucleotide encoding a monocot (monocotyledon)-derived protein having a function of improving disease resistance of a monocot and a promoter having a function of regulating expression of the polynucleotide so that the monocot will have both disease resistance and good agronomic traits; and transgenic plants comprising the nucleic acid construct and having improved resistance to the monocot disease. The present invention also relates to methods for improving disease resistance of a monocot, which utilize the nucleic acid constructs.

BACKGROUND ART

In crop production, there is a steady demand for stable production of high-quality plants and reduction of pesticide dependency. To that end, researchers are actively improving, breeding, and developing cultivars of plants resistant to pests and pathogenic microbes through useful plant biotechnologies, such as plant cell fusion and recombinant DNA techniques. Transgenic plants resistant to herbicides (Patent Document 1), viruses (Patent Document 2), and pests (Patent Document 3) have already been produced using recombinant DNA techniques. Furthermore, as listed below, several types of transgenic plants resistant to plant pathogenic microbes have been produced: transgenic plants showing resistance to pathogenic filamentous fungus, produced by introducing a gene of an enzyme which inactivates a toxin produced by the pathogenic fungus (Non-Patent Document 1); transgenic plants showing resistance to at least one pathogenic bacterium, produced by introducing a gene of an antibacterial protein derived from an insect (Patent Document 4); transgenic plants resistant to complex disease, produced by introducing a Japanese mustard spinach-derived gene (Patent Document 5); transgenic plants resistant to multiple diseases produced using the thionine gene (Patent Document 6); and transgenic plants resistant to complex disease produced using an acidic thaumatin-like protein gene (Patent Document 7). However, it is generally accepted that disease resistance achieved by introducing a single resistance gene is not sufficiently effective. Furthermore, some of the introduced genes have harmful effects on the growth, fertility, and such of the transformants, thereby hindering their practical application.

WRKY transcription factors have been reported to be involved in disease resistance of dicots such as *Arabidopsis* (Non-Patent Documents 2 to 6). Several OsWRKY genes of rice plants that confer disease resistance have been reported in recent years (Non-Patent Documents 7 to 14), but identification of genes with stronger disease resistance effects has been desired.

So far, the present inventors have isolated the OsWRKY45 gene that, upon overexpression, imparts to rice plants complex disease resistance (for example, resistance against rice blast caused by filamentous fungi or bacterial leaf blight caused by bacteria), and have succeeded in producing recombinant rice plants which overexpress OsWRKY45 using a maize ubiquitin promoter ($P_{maize\ Ubi}$) (Patent Document 8 and Non-Patent Document 15). However, when OsWRKY45 was overexpressed using the maize ubiquitin promoter, although strong resistance (complex resistance) against complex diseases was imparted to recombinant rice plants, phenomena such as growth retardation was found to occur depending on the cultivation conditions (Non-Patent Document 15).

Prior art documents relating to the present invention are shown below:

[Patent Document 1] Japanese Patent Application Kokai. Publication No. (JP-A) H02-186925 (unexamined, published Japanese patent application)
[Patent Document 2] JP-A (Kokai) H04-330233
[Patent Document 3] JP-A (Kokai) H03-247220
[Patent Document 4] JP-A (Kokai) H07-250685
[Patent Document 5] JP-A (Kokai) 2004-329215
[Patent Document 6] JP-A (Kokai) 2003-88379
[Patent Document 7] JP-A (Kokai) 2003-199448
[Patent Document 8] WO 2006/126671
[Non-Patent Document 1] Windhovel, U. et al., Plant Physiol., 104, 119-125 (1994)
[Non-Patent Document 2] Kalde, M. et al., Mol. Plant Microbe Interact., 16, 295-305 (2003)
[Non-Patent Document 3] Li, J. et al., Plant Cell, 16, 319-331 (2004)
[Non-Patent Document 4] Robatzek, S. et al., Genes Dev., 16, 1139-1149 (2002)
[Non-Patent Document 5] Yu, D. et al., Plant Cell, 13, 1527-1540 (2001)
[Non-Patent Document 6] Chen, C. et al., Plant Physiol., 129, 706-716 (2002)
[Non-Patent Document 7] Xie, Z. et al., Plant Physiol., 137, 176-189 (2005)
[Non-Patent Document 8] Qiu, Y. et al., Chinese Science Bulletin, 49(20), 2159-2168 (2004)
[Non-Patent Document 9] Qiu, D. et al., Mol Plant Microbe Interact, 20(5), 492-499 (2007)
[Non-Patent Document 10] Liu, X. et al., J Plant Physiol, 164(8), 969-979 (2007)
[Non-Patent Document 11] Chujo, T. et al., Biochimica et Biophysica Acta (BBA)—Gene Structure and Expression, 1769(7-8), 497-505 (2007)
[Non-Patent Document 12] Chujo, T. et al., Biosci Biotechnol Biochem, 72(1), 240-245 (2008)
[Non-Patent Document 13] Tao, Z. et al., Plant Phys., 151, 936-948 (2009)
[Non-Patent Document 14] Qiu, Y. and D. Yu, Environmental and Experimental Botany, 65(1), 35-47 (2009)
[Non-Patent Document 15] Shimono, M. et al., Plant Cell, 19, 2064-2076 (2007)

DISCLOSURE OF THE INVENTION

Problems to be Solved by the Invention

The present invention was achieved in view of the above circumstances. An objective of the present invention is to produce a recombinant monocot having complex disease resistance without affecting its growth or yield of a propagule (seeds).

More specifically, a problem to be solved by the present invention is to: provide a nucleic acid construct that comprises a polynucleotide encoding a monocot-derived protein having a function of improving disease resistance of a monocot and a promoter having a function of regulating expression of the polynucleotide so that it has both disease resistance and good agronomic traits; and also to provide a transgenic plant comprising the nucleic acid construct and having improved resistance to the monocot disease. Another problem to be solved is to provide a method for improving disease resistance of a monocot, which utilizes the nucleic acid construct.

Means for Solving the Problems

To solve the above-mentioned problems, the present inventors isolated many promoters having various expression characteristics from monocots, connected the OsWRKY45 gene downstream of these promoters, and then re-introduced them into monocots (rice plants), and thereby strived to produce a rice line that had both complex disease resistance and excellent agronomic traits. As a result, rice lines expressing the OsWRKY45 gene at various levels were obtained (FIGS. 1 and 3). Of these, significant resistance against rice blast and bacterial leaf blight were seen in rice plants made to express OsWRKY45 using the upstream sequence of the OsUbi1, eEF1α, or OsUbi7 gene ($P_{OsUbi1}$, $P_{EF1\alpha}$, $P_{OsUbi7}$) as the promoter (FIG. 4). Furthermore, in a greenhouse where the air temperature and humidity mimic the external environment, the rice plants expressing OsWRKY45 using $P_{OsUbi7}$ showed growth (plant height and number of effective tillers) and yield which was far better than rice plants expressing OsWRKY45 from $P_{maize\ Ubi}$ and was comparable to the non-transgenic rice plant (FIGS. 5 and 6). $P_{EF1\alpha}$ showed satisfactory results second to $P_{OsUbi7}$. These results show that the present invention enabled production of rice with complex resistance properties, which would have practical utility.

Specifically, the present inventors succeeded in producing transgenic plants having both disease resistance and good agronomic traits by combining an appropriate promoter to a transcription factor gene that improves disease resistance of a monocot, and completed the present invention.

More specifically, the present invention provides [1] to [16] below:

[1] a nucleic acid construct comprising
a polynucleotide of any one of (a) to (d) below, which encodes a monocot-derived protein having a function of improving disease resistance of a monocot, and
a promoter having a function of regulating expression of the polynucleotide so that the monocot will have both disease resistance and good agronomic trait of the monocot:
  (a) a polynucleotide encoding a protein comprising the amino acid sequence of SEQ ID NO: 2;
  (b) a polynucleotide comprising a coding region of the nucleotide sequence of SEQ ID NO: 1;
  (c) a polynucleotide encoding a protein comprising an amino acid sequence with one or more amino acid substitutions, deletions, additions, and/or insertions in the amino acid sequence of SEQ ID NO: 2; and
  (d) a polynucleotide which hybridizes under stringent conditions with a complementary strand of a polynucleotide comprising the nucleotide sequence of SEQ ID NO: 1;
[2] the nucleic acid construct of [1], wherein the promoter is a promoter having a function of regulating the relative value of an amount of expression of the aforementioned polynucleotide in a plant with respect to an amount of expression of endogenous OsUbi1 of the plant to between 0.95 and 0.17;
[3] the nucleic acid construct of [1] or [2], wherein the promoter is a ubiquitin promoter of a rice plant or a peptide elongation factor gene promoter of a rice plant;
[4] the nucleic acid construct of any one of [1] to [3], wherein the promoter is a polynucleotide comprising the nucleotide sequence of SEQ ID NO: 3 or 5;
[5] the nucleic acid construct of any one of [1] to [4], wherein the disease of a monocot is a filamentous fungal disease;
[6] the nucleic acid construct of any one of [1] to [4], wherein the disease of a monocot is a bacterial disease;
[7] a vector comprising the nucleic acid construct of any one of [1] to [6];
[8] a host cell into which the vector of [7] has been introduced;
[9] a plant cell into which the vector of [7] has been introduced;
[10] a transgenic plant comprising the plant cell of [9];
[11] a transgenic plant which is a progeny or a clone of the transgenic plant of [10];
[12] a propagule of the transgenic plant of [10] or [11];
[13] a method for producing a transgenic plant, comprising the steps of introducing the nucleic acid construct of any one of [1] to [6] into a plant cell, and regenerating a plant from the plant cell;
[14] a method for improving disease resistance of a monocot, comprising the step of expressing the nucleic acid construct of any one of [1] to [6] in a monocot cell;
[15] an agent for improving disease resistance of a monocot, comprising the nucleic acid construct of any one of [1] to [6], or the vector of [7] as an active ingredient; and
[16] a food and drink composition and a processed product, comprising the transgenic plant of [10] or [11], or the propagule of [12].

MODES FOR CARRYING OUT THE INVENTION

Figure 1:
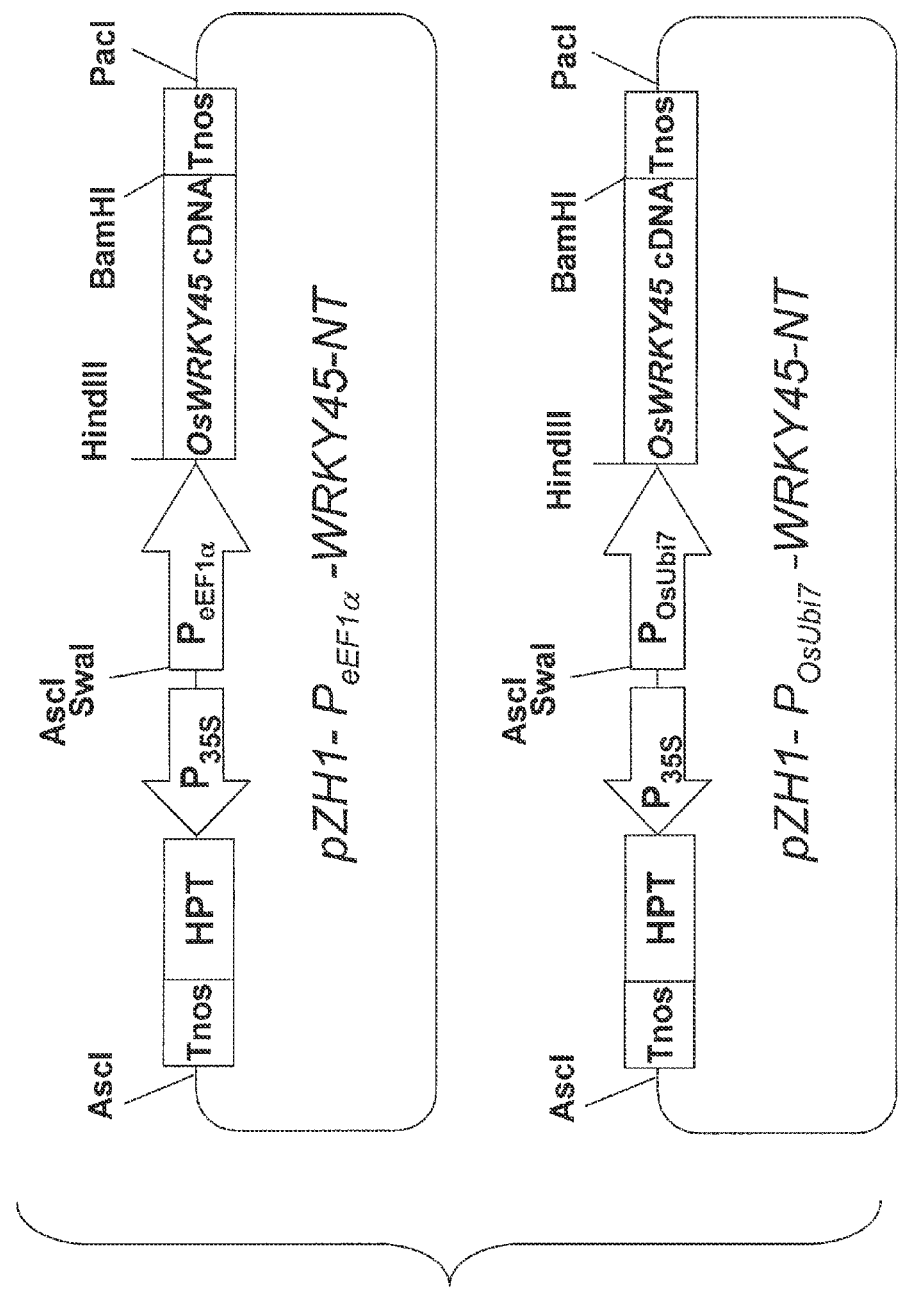
FIG. 1 shows the structures of the OsWRKY45 constitutive expression transformation vectors. HPT indicates hygromycin phosphotransferase; Tnos indicates the Nos terminator; and P35S indicates the cauliflower mosaic virus 35S promoter.

The present invention provides nucleic acid constructs that comprises a polynucleotide encoding a monocot-derived protein having a function of improving disease resistance of a monocot and a promoter having a function of regulating expression of the polynucleotide so that the monocot will have both disease resistance and good agronomic traits.

In the present invention, the phrase "disease of a monocot (monocot disease)" refers to any physiological disorder in plants which is caused by pathogens such as filamentous fungi (mainly molds), bacteria, or viruses, and which may reduce agricultural production and damage ecological environment. Pathogens are not particularly limited, and in addition to the aforementioned three pathogens, diseases caused by actinomycetes, algae, phytoplasma (plant pathogenic microorganism), and such also exist.

In the present invention, monocots which are diseased are not particularly limited; however, are preferably gramineous plants and more preferably rice plants.

Hereinafter, three typical pathogens of diseases of monocots (filamentous fungi, bacteria, and viruses) and symptoms of diseases caused by these pathogens are described. Although a "disease" in the present invention is not particularly limited, it may be any one of the diseases described below.

Filamentous fungi are microorganisms composed of multicellular "hyphae" and proliferate by totaling spores. Since they have a rigid cell wall made of chitin, they are considered to be highly resistant to drugs. Based on their shape and characteristics, filamentous fungi are classified Phycomycetes (molds), Deuteromycetes (molds), Ascomycetes (molds/mushrooms), or Basidiomycetes (mushrooms). Phycomycetes are further divided into Mastigomycotinas and Zygomycetes.

Diseases caused by filamentous fungi present a variety of symptoms, including blotch formation on stem and leaf, rot, induction of dieback by impairing base of aerial part or root, formation of swellings such as gal, etc. As a major tendency of symptoms caused by filamentous fungi, growth of powdery molds and formation of granular black substances (sclerotia=mass of hyphae) are often observed in the affected sites. Typical filamentous fungal disease in rice plants include diseases caused by *Pseudocochliobolus lunatas, Rhizoctonia oryzae-sativae, Sclerophthora macrospora, Metasphaeria aibescens, Waitea circinata, Dreschslera gigantea, Entyloma dactylidis Bipolaris oryzae, Chromelosporium fulvum, Magnaporthe salvinii, Peziza ostracoderma, Tilletia barclayana,* and *Rhizoctonia oryzae.* Rice blast disease, a symptom model in the Examples, also corresponds to a filamentous fungous disease; however, the symptoms are not limited thereto.

Bacteria are microorganisms composed of a single cell that have various shapes according to species. Bacteria swim to move in water, and invade plant bodies through wounds formed on the stub, stomata on the underleaf, etc. Bacterial diseases include those rotting stem and leaf, inducing an acute dieback, forming a tumorous swelling, etc. A common symptom includes a somewhat blurred contour of a blotch and yellowish discoloration in its periphery. Typical bacterial diseases in rice include rice bacterial brown stripe, rice bacterial leaf blight, rice bacterial palea browning, rice bacterial grain rot, and rice bacterial seedling blight. Rice bacterial leaf blight, a symptom model in the Examples, corresponds to abacterial disease; however, the symptoms are not limited thereto.

Viruses are basically composed of nucleic acids and proteins, and have various shapes depending on species. Viruses have only either one of DNAs or RNAs, and cannot proliferate unless they invade cells of other organisms and utilize their nucleic acid synthesis/protein synthesis functions. Also known are viroids that resemble viruses in characteristics and cause similar diseases. Viroids contain only RNAs and have no proteins in their nucleic acid portions, and they are smaller than viruses in size. Diseases caused by viruses and viroids are, in most cases, accompanied by mosaic symptoms having pale patchy patterns in leaves and flowers, malformations such as dwarf and deformation, small brown necrotic spots, and such. In addition, the whole plant may become yellow and dwarf, resulting in a significant growth inhibition. Typical viral diseases in rice include rice black-streaked dwarf, rice transitory yellowing disease, and rice dwarf disease.

In the present invention, the phrase "improve disease resistance of a monocot" means to confer a monocot a trait/effect in which symptoms of the aforementioned diseases do not occur or hardly occur by expressing the nucleic acid construct of the present invention in the monocot. This phrase also corresponds to a trait/effect of improving resistance to pathogens and reducing their infection.

The effect of improving disease resistance may continuously last during the lifetime of monocots or may be expressed for a certain period of time (for example, only at the early growth stage).

In addition, the disease resistance may be to a plurality of pathogens or only to a specific pathogen.

A "monocot-derived protein having a function of improving disease resistance of a monocot" of the present invention can be preferably a transcription factor, or more preferably a WRKY-type transcription factor.

The nucleotide sequence of a cDNA of a transcription factor gene of the present invention and the amino acid sequence of a protein encoded by the polynucleotide are set forth in SEQ NOs: 1 and 2, respectively.

Since the transcription factors of the present invention function to improve disease resistance of a monocot, it is possible to grow a monocot with pathogen resistance by transforming the plant with the polynucleotide encoding the protein.

The present invention includes polynucleotides that encode proteins functionally equivalent to the transcription factor protein set forth in SEQ ID NO: 2. Herein, the phrase "functionally equivalent to a transcription factor protein" means the protein has the function to improve disease resistance of a monocot. Such polynucleotides are preferably derived from gramineous plants, more preferably rice plants.

Such polynucleotides include mutants, derivatives, alleles, variants, and homologs that encode the proteins comprising, for example, an amino acid sequence having one or more amino acid substitutions, deletions, additions, and/or insertions in the amino acid sequence of SEQ NO: 2.

A method well known to those skilled in the art for preparing a polynucleotide encoding a protein having a modified amino acid sequence includes, for example, the site-directed mutagenesis method. Mutation of the amino acid sequence of a protein due to the mutation the coding nucleotide sequence may also occur in nature. Even polynucleotides encoding a protein having an amino acid sequence with one or more amino acid substitutions, deletions, or additions in the amino acid sequence encoding natural transcription factor proteins are included in the polynucleotides of the present invention, as long as the polynucleotides encode proteins functionally equivalent to a natural transcription factor protein (SEQ ID NO: 2). Furthermore, even when nucleotide sequences are mutated, the mutations do not necessarily involve amino acid mutations in proteins (degeneracy mutation). Such degeneracy mutants are also included in the polynucleotides of the present invention.

Whether or not a polynucleotide encodes a protein that functions to improve plant disease resistance can be assessed by the method described below. The most common method is a procedure in which a known pathogen found to cause a disease is added to a plant introduced with the polynucleotide and subsequent symptoms are examined while cultivating the plant in a growth chamber. Despite the addition of pathogen, when no disease symptom appears, it is shown that the introduced polynucleotide encodes a protein having the function to improve plant disease resistance. Even when the disease symptoms are suppressed or reduced, it can be interpreted that a polynucleotide encoding a protein having the function to improve plant disease resistance has been introduced.

Other methods well known to those skilled in the art for preparing polynucleotides encoding proteins functionally equivalent to the transcription factor protein net forth in SEQ ID NO: 2 include methods using hybridization techniques and polymerase chain reaction (PCR) techniques. That is, those skilled in the art can usually isolate polynucleotides highly homologous to a transcription factor gene from rice and other plants by using the nucleotide sequence of a transcription factor gene (SEQ ID NO: 1) or a portion thereof as a probe, or using an oligonucleotide that specifically hybridizes to the transcription factor gene (SEQ ID NO: 1) as a primer. Such polynucleotides encoding proteins functionally equivalent to a transcription factor protein that can be isolated by hybridization techniques and PCR techniques are also included in the polynucleotides of the present invention.

In order to isolate such polynucleotides, hybridization reaction is preferably performed under stringent conditions. The stringent hybridization conditions in the present invention refer to the condition of 6M urea, 0.4% SDS, and 0.5×SSC or conditions of similar stringency. Isolation of more highly homologous polynucleotides can be expected using a more stringent condition, for example, a condition of 6M urea, 0.4% SDS, and 0.1×SSC. The DNAs thus isolated are thought to have a high homology to the amino acid sequence (SEQ ID NO: 2) of a transcription factor protein on the amino acid level. "High homology" refers to a sequence identity of at least 50% or more, more preferably 70% or more, or even more preferably 90% or more (for example, 95%, 96%, 97%, 98%, or 99% or more) in the whole amino acid sequence. The amino acid sequence identity or nucleotide sequence identity can be determined by using the BLAST algorithm developed by Karlin and Altschul (Proc. Natl. Acad. Sci. USA 87:2264-2268, 1990; and Proc. Natl. Acad. Sci. USA 90(12), 5873, 1993). Programs referred to as BLASTN and BLASTX, which are based on the BLAST algorithm, have been developed (Altschul, S. F. et al., J. Mol. Biol. 215:403, 1990). To analyze nucleotide sequences by BLASTN, the parameters are set at, for example, score=100 and word length=12. On the other hand, the parameters used for the analysis of amino acid sequences by BLASTX are set at, for example, score=50 and word length=3. When using BLAST and Gapped BLAST programs, the default parameters are used for each program. Specific techniques for such analyses are known in the art.

Promoters used in the present invention are those having a function of regulating the expression of polynucleotides encoding a monocot-derived protein having a function of improving disease resistance of a monocot, so that the monocot has both disease resistance and good agronomic traits.

In the present invention, a polynucleotide encoding a monocot-derived protein having a function of improving disease resistance of a monocot is preferably operably linked downstream of the above-mentioned promoter. Through the activation of the above-mentioned promoter, the protein and the polynucleotide encoding the protein can be expressed in host cells, plant cells, transgenic plants, or propagules of the transgenic plants.

The activity of the above-mentioned promoters can be examined by those skilled in the art, for example, using well-known reporter assays with reporter genes. The reporter genes are not particularly limited as long as their expression is detectable, and include the CAT gene, lacZ gene, luciferase gene, β-glucuronidase gene (GUS), and GFP gene, which are generally used by those skilled in the art. The expression level of the reporter genes can be measured according to the type of the reporter genes by methods well known to those skilled in the art. For example, when the reporter gene is the CAT gene, the expression level of the reporter gene can be measured by detecting the acetylation of chloramphenicol catalyzed by the gene product. When the reporter gene is the lacZ gene, luciferase gene, β-glucuronidase gene (GUS), or GFP gene, the expression level of the reporter gene can be measured by, respectively, detecting tho color development of pigment compound as a result of the catalytic action of the gene expression product; detecting the fluorescence of fluorescent compound as a result of the catalytic action of the gene expression product; detecting the luminescence of Glucuron (ICN) or the color development of 5-bromo-4-chloro-3-indolyl-β-glucuronide (X-Gluc) as a result of the catalytic action of the gene expression product; or detecting the fluorescence of the GFP protein.

In the present invention, the phrase "operably linked" means that a promoter of the present invention and a polynucleotide encoding a protein are linked in a manner that the expression of the downstream polynucleotide which encodes the protein is induced by the binding of transcription factors to the promoter of the present invention. Therefore, even if the polynucleotide encoding the protein is bound to a different gene and forms a fusion protein with the product of this different gene, such will be included in the meaning of the above-mentioned "operably linked", as long as the expression of the fusion protein is induced through the binding of transcription factors to the promoter of the present invention.

In the present invention, the phrase "have both disease resistance and good agronomic trait(s) of the monocot" means that the monocot has the above-mentioned disease resistance (properties showing improved resistance to a disease), and at the same time, has a comparable or even improved agronomic trait compared to that of a naturally-derived monocot. In the present invention, having "a comparable or improved agronomic trait compared to that of a naturally-derived monocot" means that the sizes, total weight, number, and such of various organs (tissues) of plants such as panicles, culms, seeds, unhulled kernels, rice grains, cariopsides, tillers, and spicules, are comparable or are increased compared to those of a naturally-derived monocot Furthermore, in the present invention, having "a comparable or improved agronomic trait to that of a naturally-derived monocot" means that a trait relating to the organs (tissues) (for example, the number and sizes of panicles and culms of rice, maize, and such, and the number and size, and also the variation in shape, and colors, and such of the seeds (endosperm) of rice, maize, and such) is equivalent or improved.

Evaluation of the agronomic traits mentioned above can be carried out, for example for the panicles and culms of rice plants by planting or seeding transgenic gramineous plants or T1 or T2 seeds obtained by self-pollination of the transgenic gramineous plants in a suitable growth medium or soil, growing them under long-day conditions (day/night: 16 hour/8 hour day length) at 20° C. to 30° C., and then examining the number, sizes, shapes, and such of the panicles and culms (for example, tillers). Furthermore, the inflorescence, cariopsides, seeds, grains, unhulled rice kernels, and rice grains of rice plants can be evaluated by planting transgenic gramineous plants or seeding their T1 or T2 seeds obtained by self-pollination of the transgenic gramineous plants in a suitable growth medium or soil, growing them under long-day conditions (day/night: 16 hour/8 hour day length) at 20° C. to 30° C., and then examining the number, sizes, shapes, and such of the inflorescence, cariopsides, seeds, grains, unhulled rice kernels, and rice grains. Cultivation of monocots can be carried out in a closed-system or a non-closed-system greenhouse, a growth chamber (with completely artificial light), a glass greenhouse in which the temperature and humidity mimic the air temperature and humidity of outdoors (an artificial rice paddy), or an experimental farm.

Preferred examples of promoters of the present invention include promoters having the function of regulating the relative value of "the amount of expression of a polynucleotide of the present invention in a plant" to "the amount of expression of endogenous OsUbi1 in the plant" to less than 1, In the present invention "endogenous OsUbi1" is the rice ubiquitin 1 gene (also referred to as Rubq1) and refers to the gene registered at Genbank as DDBJ Accession No. AK121590. The amount of expression of "endogenous OsUbi1" is measured by real time quantitative RT-PCR analyses (the standard curve method) and such, and is used as the control for the amount of expression. In the present invention, the "relative value" is calculated as the "relative value" with respect to the amount of expression of "endogenous OsUbi1" in a plant, and the proportion of the amount of expression (expression level) of the aforementioned polynucleotide from the promoter is calculated by defining the amount of expression of "endogenous OsUbi1" in the plant as 1. Measurement of the amount of expression of the endogenous OsUbi1 gene or the aforementioned polynucleotide by the promoter can be carried out by methods known to those skilled in the art. For example, by extracting the mRNA of the gene or the aforementioned polynucleotide by a standard method, the amount of expression of the gene or the aforementioned polynucleotide can be measured by performing the RT-PCR method (for example, the real time quantitative RT-PCR analysis method) which uses this mRNA as the template or the northern hybridization method. The above-mentioned "relative value" is not particularly limited as long as it is less than 1; however, it is, for example, preferably in the range of 0.99 to 0.10, and more preferably in the range of 0.95 to 0.17.

Preferred examples of the promoters of the present invention include the ubiquitin promoters of rice plants or peptide elongation factor gene promoters of rice plants.

More preferred examples of the promoters of the present invention include the OsUbi7 gene promoters or the eEF1α gene promoters. More specifically, the promoters of the present invention include, for example, the following polynucleotide of (a) or (b):
(a) a polynucleotide comprising the nucleotide sequence set forth in SEQ ID NO: 3 or 5; or
(b) a polynucleotide which hybridizes under stringent conditions with a complementary strand of a polynucleotide comprising the nucleotide sequence set forth in SEQ ID NO: 3 or 5.

The nucleic acid constructs of the present invention can, he used, for example, in the production of transgenic plants with improved disease resistance and the preparation of recombinant proteins.

For producing transgenic plants having improved plant disease resistance using the nucleic acid constructs of the present invention, the nucleic acid constructs of the present invention are inserted into appropriate vectors, and then the vectors are introduced into plant cells to regenerate the transgenic plant cells thus obtained. The transcription factor gene isolated by the present inventors has the function to improve plant disease resistance, and it is possible to introduce this transcription factor gene into an arbitrary plant variety and regulate its expression using a promoter, thereby improving disease resistance in that variety. This transformation requires an extremely short period of time compared to the conventional gene transfer by crossing, and also has an advantage in involving no alteration in other characteristics.

The present invention also provides vectors into which the above-described nucleic acid constructs of the present invention have been inserted. The vectors of the present invention include, in addition to the aforementioned vectors used for producing recombinant proteins, vectors for expressing nucleic acid constructs of the present invention in plant cells so as to produce transgenic plants. Such vectors are not particularly limited, so long as they include a terminator sequence having a polyadenylation site required for stabilization of the transcription products. The vectors include, for example, "pBI121", "pBI221", and "pBI101" plasmids (all from Clontech). Vectors used for transformation of plant cells are not particularly limited so long as they can express the inserted gene in the cells. Herein, "plant cells" include plant cells in various forms, for example, suspended cultured cells, protoplasts, leaf segments, and calluses.

The present invention also provides transgenic cells into which the vectors of the present invention have been inserted. Cells into which the vectors of the present invention are introduced include, in addition to the above-described cells used for producing recombinant proteins, plant cells for producing transgenic plants. Plant cells are not particularly limited, and include, for example, cells of rice, *Arabidopsis*, corn, potato, and tobacco. Plant cells of the present invention include, in addition to cultured cells, cells in plants as well as protoplasts, shoot primordia, multiple shoots, and hairy roots. The vectors can be introduced into plant cells using various methods known to those skilled in the art, such as the polyethylene glycol method, electroporation method, a method via Agrobacterium, and the particle gun method. Regeneration of a plant from transgenic plant cells can be performed by methods known to those skilled in the art depending on the type of plant cell. For example, in rice, several techniques for producing transgenic plants have been already established, including the following: a method for introducing a gene into a protoplast with polyethylene glycol to regenerate a plant (suitable for indica rice varieties); a method for introducing a gene into a protoplast with electrical pulse to regenerate a plant (suitable for japonica rice varieties); a method for directly introducing acne into a cell by the particle gun method to regenerate a plant; and a method for introducing a gene into a cell via *Agrobacterium* to regenerate a plant and so on. These methods are widely used in the technical field of the present invention. In this invention, these methods can be preferably used.

Transgenic plant cells can regenerate plants by redifferentiation. Methods for redifferentiation vary depending on the type of plant cell. The methods include, for example, the method of Fujimura et al. (Plant Tissue Culture Lett. 2: 74 (1995)) for rice; the method of Shillito et al. (Bio/Technology 7: 581 (1989)) and the method of Gorden-Kamm et al. (Plant Cell 2: 603 (1990)) for corn; the method of Visser et al. (Theor. Appl. Genet 78: 594 (1989)) for potato; the method of Nagata and Takebe (Planta 99: 12 (197))) for tobacco; the method of Akama et al. (Plant Cell Reports 12: 7-11 (1992)) for *Arabidopsis;* and the method of Dohi et al. (JP-A (Kokai) H08-89113) for eucalyptus.

Once a transgenic plant in which a DNA of the present invention has been introduced into the genome is obtained, its progeny can be obtained from the plant by sexual or asexual reproduction. It is also possible to obtain propagules (such as seeds, fruits, panicles, tubers, root tubers, stubs, calluses, and protoplasts) from the plant and its progenies or clones and to mass-produce the plant based on these materials. The present invention encompasses plant cells into which the DNAs of the present invention have been introduced; plants comprising such cells, progenies and clones of the plants, as well as propagules of the plants and their progenies and clones.

The monocots having improved disease resistance thus produced have improved pathogen resistance compared to wild-type monocots. For example, it was found that the monocots into which the DNA encoding a transcription factor OsWRKY45 had been introduced showed extremely strong resistance to the blast fungus. Use of the techniques of the present invention enables pesticide-free production of rice, which is a useful agricultural product, and may lead to the prevention of environmental destruction and improved productivity.

The present invention relates to agents which improve plant disease resistance, comprising the nucleic acid construct or the vector as an active ingredient.

In the agents of the present invention, sterilized water, physiological saline, vegetable oil, surfactants, lipids, solubilization agents, buffers, preservatives, and such may be mixed in when necessary, in addition to the active ingredients, that is, the nucleic acid constructs or the vectors.

Furthermore, the present invention provides food and drink compositions and processed products comprising the aforementioned transgenic plants or transgenic propagules of the present invention. Examples of the propagules of the monocots of the present invention (for example, rice plants) include propagules of rice. The rice of the present invention can have the same uses as ordinary rice. For example, the rice itself can have edible use by subjecting it to treatments such as cooking, boiling, frying, steaming, or deep-frying. Furthermore, it can be used in combination with food and drink compositions other than rice. For example, it can be used in takikomi gohan (seasoned rice and cooked with meat, fish, and/or vegetables), zosui (rice soup with meat, fish, and/or vegetables), fried rice, and such. Furthermore, by grinding rice, it can be used as a process material for rice flour, glutinous rice flour, udon noodles, soba noodles, spaghetti, macaroni, rice vermicelli, bread, rice snacks such as rice crackers, arare crackers (grilled pieces of rice cakes), cookies, and the like. Furthermore, it may be used as a material for extracting rice oil and such. It can also be used as a raw material for brewing, fermentation, or such. Rice bran may also be used for the purpose of pickling food and drink products. Needless to say, the transgenic plants or transgenic propagules of the present invention may be used not only for humans, but also as animal feed (for example, pet food). Furthermore, the food and drink compositions and processed products may be in forms placed in containers and packaging. For example, food and drink products in forms enclosed in containers such as plastic-molded containers, or those enclosed in containers such as retort pouches, sealed, and then sterilized are included in the present invention. That is, the purposes and methods of using the transgenic plants or transgenic propagules of the present invention are not particularly limited.

All documents cited herein are incorporated by reference in their entirety.

EXAMPLES

Herein below, the present invention will be specifically described using Examples; however, it is not to be construed as being limited thereto.

Example 1

Vector Construction

Vectors for constitutively expressing OsWRKY45 in plants were prepared by the following procedure. A SfiI-PacI fragment derived from pZH1-Ubi-WRKY45-NT (Shimono, M. et al., Plant Cell, 19, 2064-2076 (2007)) and the complementary oligo DNA (produced by annealing the top strand: AGCTTGGCCAAAT (SEQ ID NO: 9) and the bottom strand: TGGCCA) were inserted into a HindIII-PacI site of pZH1 to construct a plasmid vector pZH1l-WRKY45-NT-1. A complementary oligo DNA (produced by annealing the top strand: AGCTGGCGCGCCAITTATA (SEQ ID NO: 10) and the bottom strand: AGCTTATTTAAATGGCGCGCC (SEQ ID NO: 11)) was inserted to the HindIII site of pZH1-WRKY45-NT-1 to construct pZH1-WRKY45-NT-2.

Ten candidates genes for obtaining promoters to be used for expressing OsWRKY45 were selected (ChaC, SADP, AAT, CBS, NONE, LTP, OsUbi1, eEF1α, OsUbi7, and ACT8) by referring to information on transcript levels and such in databases (NCBI, RiceXPro). Based on the information in a database (RAP-DB), the sequences of approximately 2 kb upstream from the translation start site of these genes were PCR-amplified using primers and inserted into HindIII-digested pZH1-WRKY45-NT-2 using an In-Fusion kit (TAKARA BIO) to construct OsWRKY45 constitutive expression transformation vectors (FIG. 1). The sequences of the PCR-amplified sequences were confirmed by sequencing. The nucleotide sequence of the $P_{OsUbi7}$-WRKY45 portion of pZH1-$P_{OsUbi7}$-WRKY45-NT (the vector into which a $P_{OsUbi7}$ promoter is inserted) is shown in SEQ ID NO: 4, the nucleotide sequence of the $P_{eEF1a}$-WRKY45 portion of pZH1-$P_{eEF1a}$-WRKY45-NT (the vector into which a $P_{eEF1a}$ promoter is inserted) is shown in SEQ ID NO: 6, and the nucleotide sequence of the $P_{OsUbi1}$-WRKY45 portion of pZH1-$P_{OsUbi1}$-WRKY45-NT (the vector into which a $P_{OsUbi1}$ promoter is inserted) is shown in SEQ ID NO: 8.

Example 2

Promoter Analysis

Figure 2:
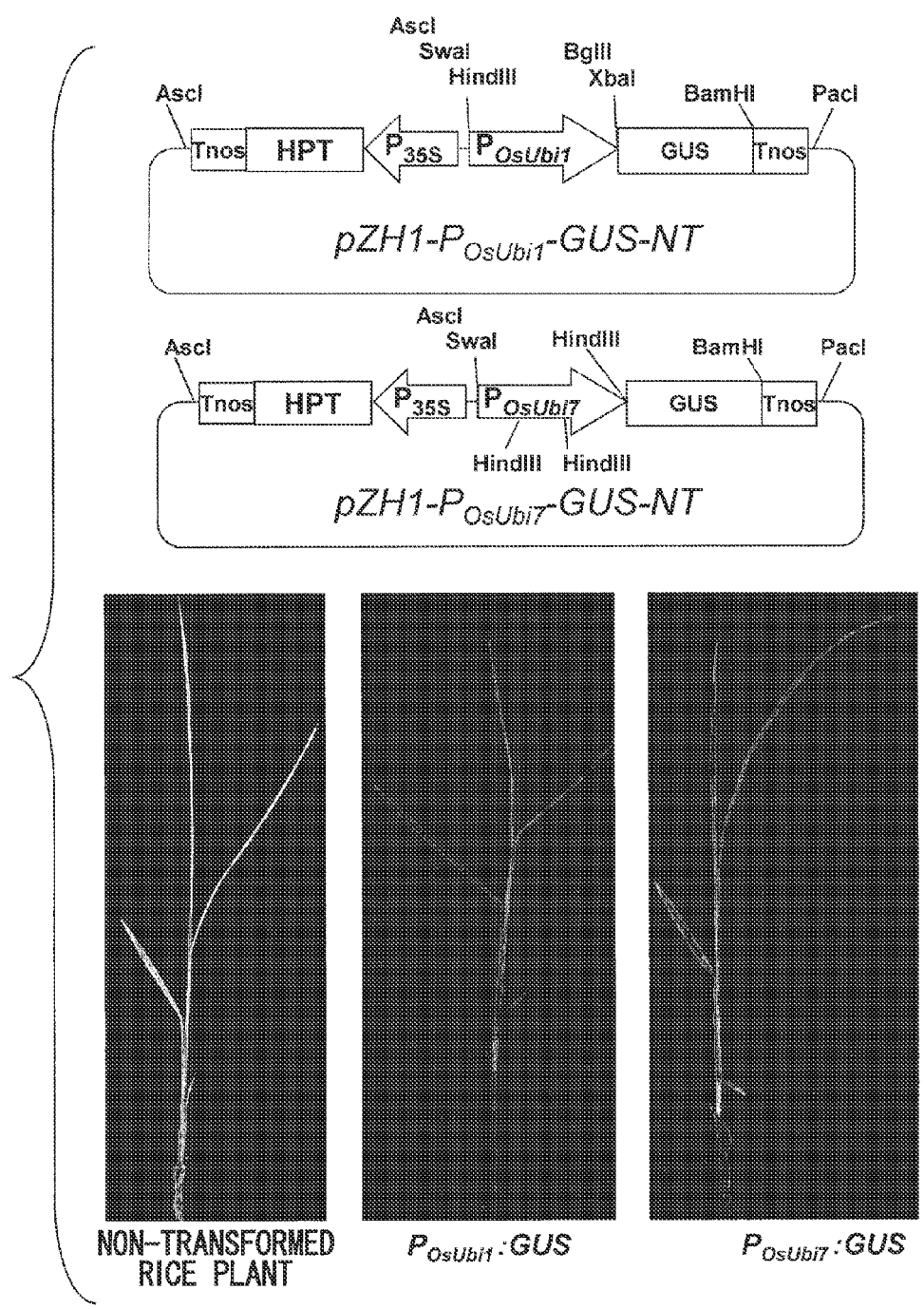
FIG. 2 shows the structures of the $P_{OsUbi1}$ promoter:GUS and $P_{OsUbi7}$ promoter:GUS transformation vectors, and indicates the results of histochemical activity staining using transgenic rice (five-leaf stage) into which each vector is introduced. GUS refers to β-glucuronidase. GUS activity was expressed in the whole plant with either promoter, and both promoters were shown to have constitutive expression activity.

To produce vectors for expressing the β-glucuronidase (GUS) reporter gene under the control of the $P_{OsUbi1}$ and $P_{OsUbi7}$ promoters (pZH1-$P_{OsUbi1}$-GUS-NT and pZH1-$P_{OsUbi7}$-GUS-NT), pZH1-$P_{OsUbi1}$-WRKY45-NT was cleaved with XbaI and BamHI, and pZH1-$P_{OsUbi7}$-WRKY45-NT was cleaved with HindIII (partial) and BamHI, and then PCR-amplified GUS fragment was inserted into the cleaved sites using an In-Fusion kit (TAKARA BIO) (FIG. 2).

Histochemical staining of GUS activity using the transgenic rice plants produced was carried out essentially according to Jefferson's method (Jefferson, R. A. (1989) "The GUS reporter gene system" Nature 342:837-838). Specifically, the staining reaction was carried out by keeping the T1 transformant rice seedlings (4.5 to 5-leaf stage) in acetone for one minute, then soaking this in a GUS staining solution (100 mM sodium phosphate buffer pH 7.0, 10 mM EDTA pH 7.0, 0.5 mM K Ferricyanide pH7.0, 0.5 mM K Ferrocyanide pH 7.0, 1 mM X-Glucuronide, 0.05% Silwet L-77), degassing fix one hour in a vacuum desiccator, and then leaving at 37° C. for 24 hours. Thereafter, the staining solution was removed, decolorized by leaving the sample in 70% ethanol at 37° C. for 24 hours, and then the staining patterns were observed.

The results of GUS staining showed staining of the whole plants in the rice lines with both promoters. These results show that when these promoters are used to express the WRKY45 gene, WRKY45 will be expressed in whole plant, indicating that it will be possible to deal with pathogen infection at various sites.

Example 3

Expression Analysis of the OsWRKY45 Transgene

Figure 3:
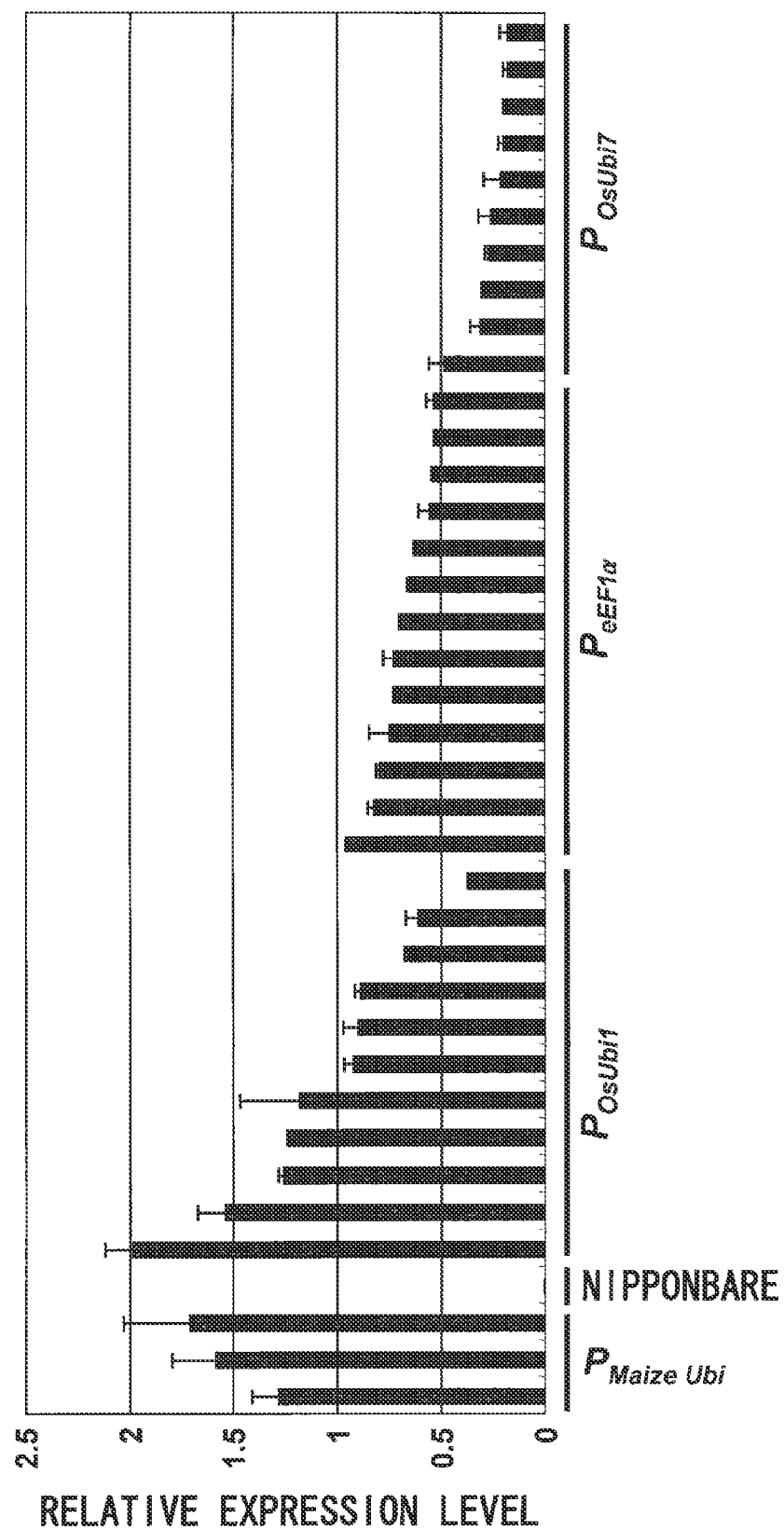
FIG. 3 shows the expression levels of the introduced OsWRKY45 in each of the transgenic rice lines. One and a half months after transplantation (T1), the completely extended leaves at the top were used for analyses. Analyses were carried out by real time PCR analyses (the standard curve method), and the results are shown as relative values with respect to the internal standard OsUbi1 gene.

To perform expression analysis of the OsWRKY45 transgene OsWRKY45 overexpressing plants, the T1 generation of the transformants produced by Agrobacterium infection and non-transformants were transplanted to potting soil (Bonsol No. 2) and cultivated in a growth chamber. One and a half months later, completely extended leaves at the top were harvested. After RNA extraction, the expression of the introduced OsWRKY45 was analyzed by real-time (RT)-PCR (FIG. 3). As primers, the forward strand TGTGT-GACAAGCAAGAGAAGAGGA. (SEQ ID NO: 12) and the reverse strand AACGATCGGGGAAATTCGAG (SEQ ID NO: 13) were used. In FIG. 3, only the expression data for the transformant lines (using the three promoters, $P_{OsUbi1}$, $P_{eEF1a}$, $P_{OsUbi7}$) that showed complex disease resistance in Examples 4 and 5 are shown.

Example 4

Rice Blast Inoculation Test

Figure 4:
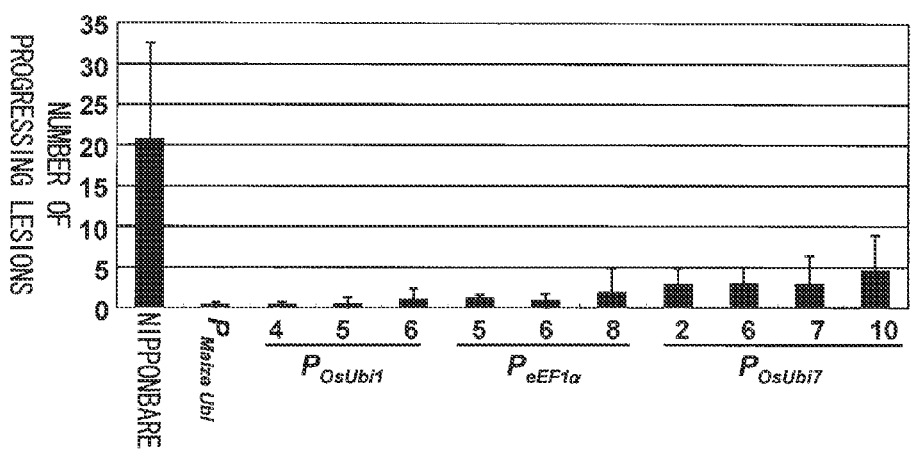
FIG. 4 shows the results of disease resistance test on novel OsWRKY45-expressing rice plants. Rice blast resistance (A) and bacterial leaf blight resistance (B) of rice plants which express OsWRKY45 by the three promoters ($P_{OsUbi1}$, $P_{eEF1\alpha}$, $P_{OsUbi7}$) are shown. The values are means of ten plants +/− standard deviation. Rice plants of T1 generation having a single insertion of the transgene in the genome (mixture of homozygotes and heterozygotes) were used.
Figure 4:
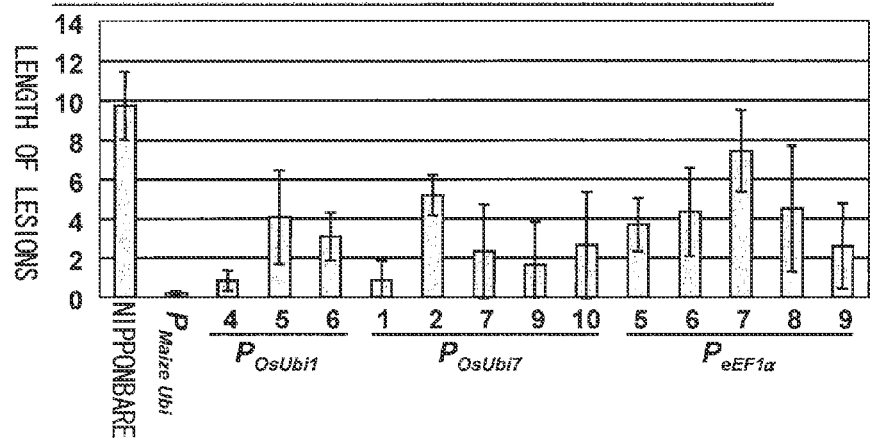

To test the change in rice blast resistance in OsWRKY45-overexpressing plants of T1 generation, seeds of non-transformants and the T1 transformants were aseptically seeded onto an MS medium and an MS medium containing 30 µg/mL of hygromycin, respectively. After culturing for five days at 30° C., they were transplanted to potting soil (Bonsol No. 2) in an isolated greenhouse. Then, to the rice seedlings (five-leaf stage) of the OsWRKY45-overexpressing plants and the non-transformants grown for 13 days, blast fungus spores (race 007, $1.0 \times 10^5$ spores/mL) were spray-inoculated, and lesion numbers over ten-centimeter length around the center of the fifth leaf were counted seven days later. As a result, in the plants overexpressing OsWRKY45 from the three promoters ($P_{OsUbi1}$, $P_{eEF1a}$, $P_{OsUbi7}$), lesion numbers due to rice blast infection were remarkably decreased compared to the non-transformants, indicating that rice blast resistance was improved in these transformants (FIG. 4). On the other hand, the transformant lines into which a construct carrying each of the seven promoters other than $P_{OsUbi1}$, $P_{eEF1a}$, and $P_{OsUbi7}$ was introduced showed weaker resistance to rice blast.

Example 5

Bacterial Leaf Blight Inoculation Test

To test the change in bacterial leaf blight resistance in OsWRKY45-overexpressing plants of T1 generation, seeds of the non-transformants and the T1 transformants were aseptically seeded onto an MS medium and an MS medium containing 30 µg/mL of hygromycin, respectively. After culturing for five days at 30° C., they were transplanted to Bonsol No. 2 in an isolated greenhouse. Then, to the OsWRKY45-overexpressing plants and the non-transformants grown for 30 days, leaf blight bacterium (T7174 strain) was inoculated by leaf-clipping inoculation using surgical scissors soaked in the bacterial suspension ($OD_{600}$=0.03). The inoculated rice plants were managed in an isolated green house. Two weeks later, the length of the lesions from the cut sites was measured. As a result, the development of lesions due to bacterial leaf blight disease was remarkably suppressed in the plants overexpressing OsWRKY45 from the three promoters ($P_{OsUbi1}$, $P_{eEF1a}$, $P_{OsUbi7}$). From these results, the OsWRKY45-overexpressing plants were found to have strong resistance against bacterial leaf blight as well (FIG. 4). On the other hand, the transformant lines into which a construct carrying each of the seven promoters other than $P_{OsUbi1}$, $P_{eEF1a}$, and $P_{OsUbi7}$ was introduced showed weaker resistance to bacterial leaf blight.

Example 6

Evaluation of Growth in Artificial Rice Paddy in a Greenhouse

Figure 5:
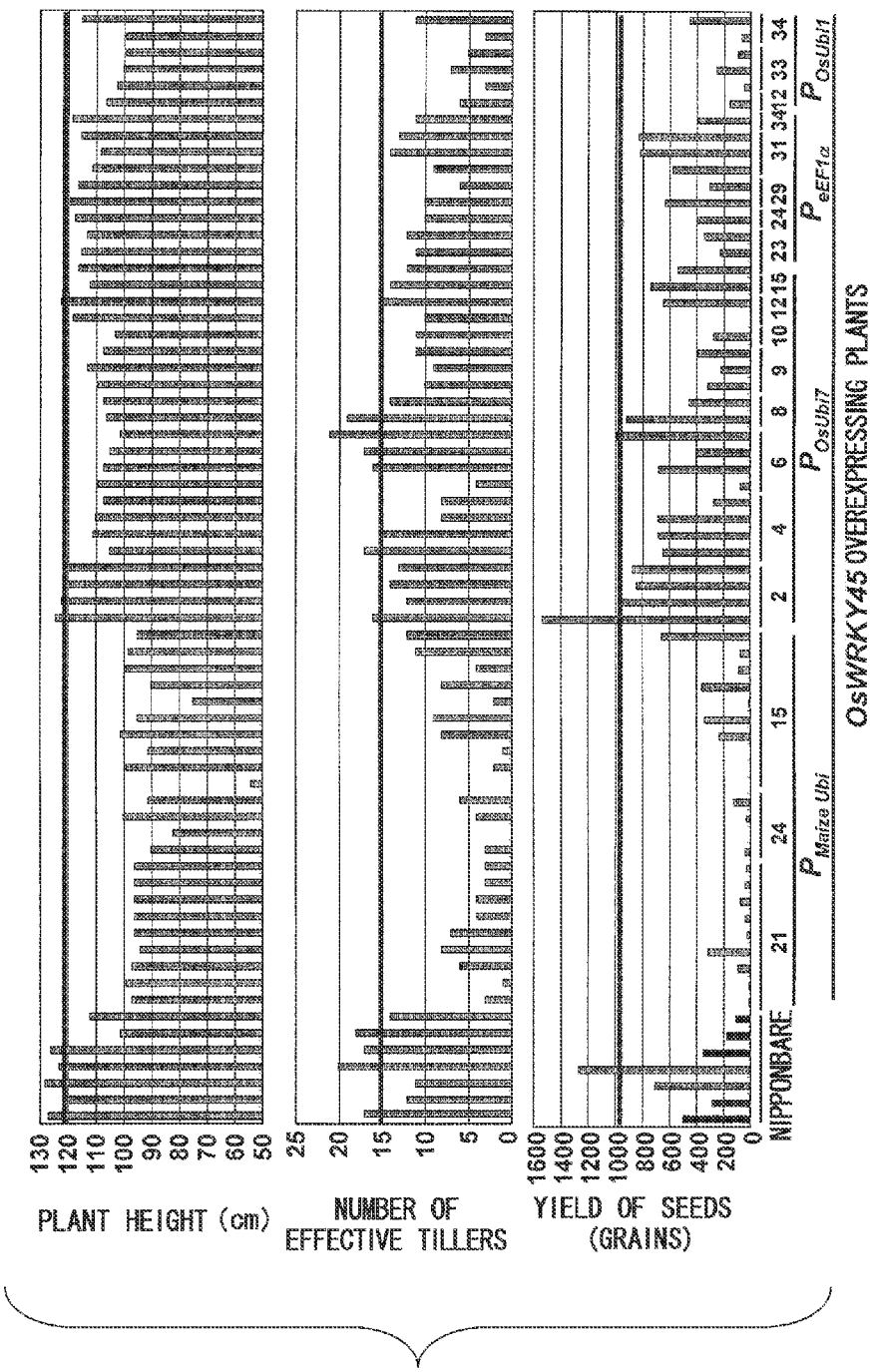
FIG. 5 shows the results of examining the growth of OsWRKY45-expressing rice plants in a greenhouse mimicking external environments. Rice plants of the T1 generation (mix of homo/hetero) having a single insertion of the transgene were cultivated from June to October, and only the results for homozygous plants, which had been determined by a homozygosity/heterozygosity determination by qPCR, are shown. The thick horizontal lines indicate the average values of control Nipponbare. Regarding the yield of seeds, brown discoloration of panicles presumably due to infection by pathogens (unidentified) was observed in some of the Nipponbare rice plants (black bars); thus, they were not included in the calculation of the yield of seeds.
Figure 6:
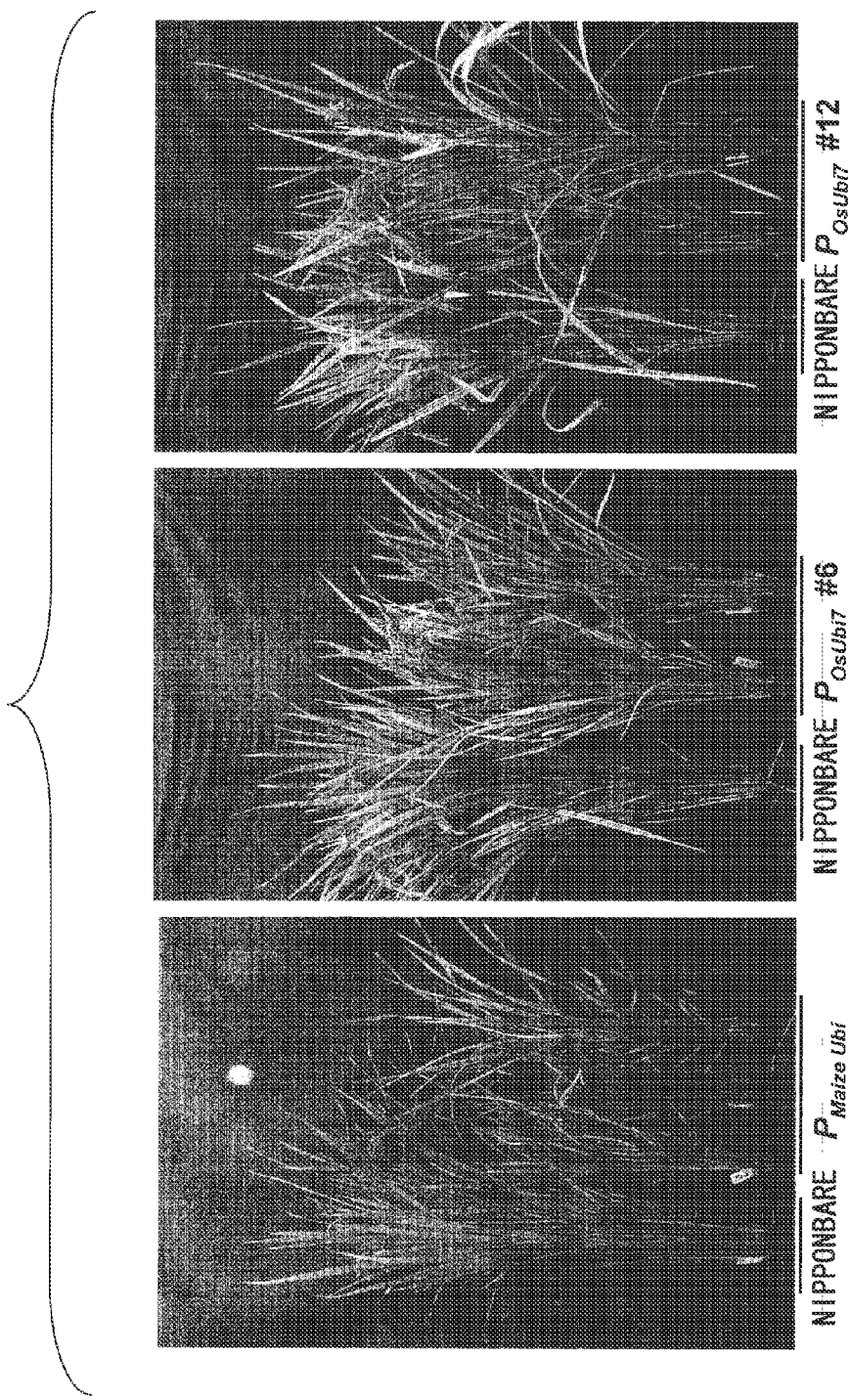
FIG. 6 provides photographs showing the growth of the OsWRKY45-expressing rice plants in a greenhouse in which temperature and humidity mimic external environments. Rice plants that express OsWRKY45 from the $P_{OsUbi7}$ or the $P_{maize\ Ubi}$ promoter (homozygoes of T1 and T4, respectively) are compared with the control Nipponbare. Representatives of those cultivated in the experiment in FIG. 5 are shown.

To evaluate good agronomic traits of the transformants under conditions close to the field environment, the transformants of T1 generation were cultivated in a glass greenhouse (an artificial rice paddy) in which temperature and humidity mimic those outside the greenhouse. On May 24, 2010, seeds of the non-transformants and the T1 transformants were aseptically seeded onto an MS medium and an MS medium containing 30 μg/mL of hygromycin, respectively. After culturing for 17 days at 30° C., the plants were transferred to Bonsol No. 2 in the artificial rice paddy. To avoid the influences of the positions in the greenhouse, the plants were rotated in positions twice a week. Plant heights and effective tiller numbers were determined on September 24. Harvesting and counting of the grain number were carried out on October 6. Homozygosity/heterozygosity of the transgenes in individual plants was determined by real-time PCR using genomic DNA and hygromycin resistance of the seedlings (sprouting/growth of the harvested seeds). As a result of these evaluations, the rice plants overexpressing OsWRKY45 from the $P_{OsUbi1}$ promoter were found to show deterioration of agronomic traits, although they were improved as compared to those overexpressing OsWRKY45 from the maize ubiquitin promoter ($P_{maizeUbi}$). On the other hand, the rice plants overexpressing OsWRKY45 from the $P_{OsUbi7}$ promoter showed far more better agronomic traits compared with those overexpressing OsWRKY45 from the maize ubiquitin promoter or the $P_{OsUbi1}$ promoter in a greenhouse (the artificial rice paddy) mimicking the natural environment; they were comparable with non-transformants (FIGS. 5 and 6). Together, these rice lines were found to be balanced between complex disease resistance and good agricultural traits at environment mimicking the natural environment, making them suitable for practical use. In addition, the rice lines overexpressing OsWRKY45 from the $P_{EF1\alpha}$ promoter showed good growth in the artificial rice paddy (greenhouse mimicking the natural environment) second to those overexpressing OsWRKY45 from the $P_{OsUbi7}$ promoter on average, and some of these lines were comparable to non-transformants (FIGS. 5 and 6).

INDUSTRIAL APPLICABILITY

In the present invention, production of transgenic plants having both disease resistance and favorable agronomic traits was successfully accomplished by highly expressing the gene of a rice transcription factor OsWRKY15 in a monocot under the control of a suitable promoter.

This technique to produce genetically modified monocots, in which complex disease resistance and good agronomic traits are balanced, provided by the present invention, may develop into practical techniques that can be utilized at sites where crops for feed, food, biofuel, etc are cultivated.

If the methods of the present invention develop into practical use, cultivation of crops with reduced use of pesticides will become possible, which would have significant effects on the costs and safety of crop production.

The invention claimed is:

1. A nucleic acid construct comprising a polynucleotide which encodes a monocot-derived protein for improving disease resistance to a disease of a monocot, and a promoter for regulating expression of the polynucleotide, wherein the protein has 98% or more identity to the amino acid sequence of SEQ ID NO: 2, and
   wherein the promoter is a polynucleotide comprising the nucleotide sequence of SEQ ID NO: 3 or 5.

2. The nucleic acid construct of claim 1, wherein the disease of a monocot is a filamentous fungal disease.

3. The nucleic acid construct of claim 1, wherein the disease of a monocot is a bacterial disease.

4. A vector comprising the nucleic acid construct of claim 1.

5. A host cell comprising the vector of claim 4.

6. The host cell of claim 5, wherein the host cell is a plant cell.

7. A transgenic plant comprising the plant cell of claim 6.

8. A transgenic plant which is a progeny or a clone of the transgenic plant of claim 7.

9. A propagule of the transgenic plant of claim 7 or 8.

10. A method for producing a transgenic plant, comprising the steps of introducing the nucleic acid construct of claim 1 into a plant cell, and regenerating a plant from the plant cell.

11. A method for improving disease resistance of a monocot, comprising the step of expressing the nucleic acid construct of claim 1 in a monocot cell.

12. An agent for improving disease resistance of a monocot, comprising the nucleic acid construct of claim 1, or the vector of claim 4 as an active ingredient.

13. A food or drink composition or a processed product, comprising the transgenic plant of claim 10, or the propagule of claim 9.

14. The nucleic acid construct of claim 1, wherein the protein has 99% or more identity to the amino acid sequence of SEQ ID NO: 2.

15. The nucleic acid construct of claim 1, wherein the polynucleotide is:
   (a) a polynucleotide encoding a protein comprising the amino acid sequence of SEQ ID NO: 2; or
   (b) a polynucleotide comprising the coding region of the nucleotide sequence of SEQ ID NO: 1.

* * * * *

UNITED STATES PATENT AND TRADEMARK OFFICE
CERTIFICATE OF CORRECTION

PATENT NO. : 9,434,958 B2
APPLICATION NO. : 14/004143
DATED : September 6, 2016
INVENTOR(S) : Hiroshi Takatsuji et al.

Page 1 of 1

It is certified that error appears in the above-identified patent and that said Letters Patent is hereby corrected as shown below:

In the Claims

Claim 13, Column 36, replace "comprising the transgenic plant of claim 10, or the propagule," with --comprising the transgenic plant of claim 7, or the propagule--.

Signed and Sealed this
Fifth Day of September, 2017

Joseph Matal
*Performing the Functions and Duties of the*
*Under Secretary of Commerce for Intellectual Property and*
*Director of the United States Patent and Trademark Office*